US010723779B2

(12) United States Patent
Gellman et al.

(10) Patent No.: US 10,723,779 B2
(45) **Date of Patent: *Jul. 28, 2020**

(54) ALPHA/BETA-POLYPEPTIDE ANALOGS OF GLUCAGON-LIKE PEPTIDE 1

(71) Applicants: Wisconsin Alumni Research Foundation, Madison, WI (US); President and Fellows of Harvard College, Cambridge, MA (US)

(72) Inventors: Samuel H. Gellman, Madison, WI (US); Lisa M. Johnson, Glendale, CA (US); Alan Attie, Madison, WI (US); Mark P. Keller, McFarland, WI (US); Alan Saghatelian, Cambridge, MA (US)

(73) Assignees: Wisconsin Alumni Research Foundation, Madison, WI (US); President and Fellows of Harvard College, Cambridge, MA (US)

( * ) Notice: Subject to any disclaimer, the term of this patent is extended or adjusted under 35 U.S.C. 154(b) by 28 days.

This patent is subject to a terminal disclaimer.

(21) Appl. No.: 15/648,937

(22) Filed: Jul. 13, 2017

(65) Prior Publication Data

US 2017/0320928 A1 Nov. 9, 2017

Related U.S. Application Data

(62) Division of application No. 14/312,081, filed on Jun. 23, 2014, now Pat. No. 9,738,697.

(60) Provisional application No. 61/838,300, filed on Jun. 23, 2013.

(51) Int. Cl.

| | |
|---|---|
| ***A61K 38/00*** | (2006.01) |
| ***A61K 38/26*** | (2006.01) |
| ***A61P 3/10*** | (2006.01) |
| ***A61P 7/12*** | (2006.01) |
| ***C07K 14/605*** | (2006.01) |
| ***C12N 5/00*** | (2006.01) |
| ***C12N 5/02*** | (2006.01) |
| ***A61K 38/02*** | (2006.01) |
| ***C07K 5/00*** | (2006.01) |
| ***C07K 7/00*** | (2006.01) |
| ***C07K 16/00*** | (2006.01) |
| ***C07K 17/00*** | (2006.01) |

(52) U.S. Cl.
CPC ............ *C07K 14/605* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 5,424,286 | A | 6/1995 | Eng | |
| 6,268,343 | B1 | 7/2001 | Knudsen et al. | |
| 6,458,924 | B2 | 10/2002 | Knudsen et al. | |
| 7,235,627 | B2 | 6/2007 | Knudsen et al. | |
| 7,268,213 | B2 | 9/2007 | Dong | |
| 8,114,833 | B2 | 2/2012 | Pedersen et al. | |
| 9,738,697 | B2 * | 8/2017 | Gellman | C07K 14/605 |
| 2008/0260838 | A1 * | 10/2008 | Hokenson | A61K 9/0075 424/489 |
| 2014/0121154 | A1 * | 5/2014 | Shandler | C07K 14/605 514/5.3 |

FOREIGN PATENT DOCUMENTS

| | | | | |
|---|---|---|---|---|
| EP | 2630965 | A1 | 8/2013 |
| WO | WO 2012/138941 | A1 | 10/2012 |

OTHER PUBLICATIONS

Foyes Medicinal Chemistry, Ed. T Lemke and D Williams, p. 898 (Year: 2013).*
Johnson L "Development of a/b Peptides as Fusion Inhibitors of HIV and Agonists of Glucagon-Like Peptide-1 Receptor (GLP-1R)" Dissertation. (Year: 2012).*
Rudat et al. "Transaminases for the synthesis of enantiopure beta-amino acids" Amb Express 12:11 (Year: 2012).*
Adelhorst et al., Structure-activity studies of glucagon-like peptide-1. *J. Biol. Chem.* 269, 6275-8, (1994).
Arkin et al., Small-molecule inhibitors of protein-protein interactions: progressing toward the dream. *Nat. Rev. Drug Discov.* 3, 301-17, (2004).
Azzarito et al., Inhibition of α-helix-mediated protein-protein interactions using designed molecules. *Nat. Chem.* 5, 161-73, (2013).
Baek, et al., Structure of the stapled p53 peptide bound to Mdm2, *J. Am. Chem. Soc.* 134, 103-6, (2012).
Berge et al., "Pharmaceutical Salts," *J. Pharm. Sci.*, 66, 1-19 (1977).
Bhatnagar et al., Positional cloning of a type 2 diabetes quantitative trait locus; tomosyn-2, a negative regulator of insulin secretion. *PLoS Genet.* 7, e1002323, (2011).
Blackwell et al., Highly efficient synthesis of covalently cross-linked peptide helices by ring-closing metathesis. *Angew. Chem. Int. Ed.* 37, 3281-4, (1998).
Boersma et al., Evaluation of diverse α/β-backbone patterns for functional α-helix mimicry: analogues of the Bim BH3 domain. *J. Am. Chem. Soc.* 134, 315-23, (2012).
Bullock et al., Assessing helical protein interfaces for inhibitor design. *J. Am. Chem. Soc.* 133, 14220-3, (2011).
(Continued)

*Primary Examiner* — James H Alstrum-Acevedo
*Assistant Examiner* — Zachary J Miknis
(74) *Attorney, Agent, or Firm* — Joseph T. Leone, Esq.; DeWitt LLP

(57) ABSTRACT

Described herein are peptide analogs of glucagon-like peptide 1 (GLP-1) that retain agonist activity, but are more resistant to proteolytic degradation than native GLP-1. In the analogs, at least one α-amino acid found in the native GLP-1 is replaced with a β-amino acid residue, which may or may not be cyclically constrained. Pharmaceutical compositions containing the analogs are described, as are methods to treat diabetes, and methods to make proteolytically resistant GLP-1 analogs.

14 Claims, 8 Drawing Sheets

Specification includes a Sequence Listing.

(56) References Cited

OTHER PUBLICATIONS

Chapman et al., A highly stable short α-helix constrained by main-chain hydrogen-bond surrogate. *J. Am. Chem. Soc.* 126, 12252-3, (2004).
Chorev et al., Cyclic parathyroid hormone related protein agonists: lysine 13 to aspartic acid 17 [i to (i+4)] side chain to side chain lactamization. *Biochemistry* 30, 5968-74, (1991).
Christel et al., Metabolic and digestive response to food ingestion in a binge-feeding lizard, the Gila monster (*Heloderma suspectum*). *The Journal of Experimental Biology* 210, 3430-9, (2007).
Davidson et al., Exenatide, *Nat. Rev. Drug Discov.* 4, 713-4, (2005).
De Menthiere et al., Structure requirements of the N-terminal region of GLP-1-[7-37]-$NH_2$ for receptor interaction and cAMP production. *Eur. J. Med. Chem.* 39, 473-80, (2004).
Deacon et al., Dipeptidyl peptidase IV resistant analogues of glucagon-like peptide-1 which have extended metabolic stability and improved biological activity. *Diabetologia* 41, 271-8, (1998).
Drucker et al., Liraglutide, *Nat. Rev. Drug Discov.* 9, 267-8, (2010).
Felix et al., Synthesis, biological activity and conformational analysis of cyclic GRF analogs. *Int. J. Peptide Protein Res.* 21, 441-54, (1988).
Foye's Principles of Medicinal Chemistry, p. 898, Published 2008.
Fredriksson et al., The G-protein-coupled receptors in the human genome form five main families. Phylogenetic analysis, paralogon groups, and fingerprints. *Mol. Pharmacol.* 63, 1256-72, (2003).
Gao et al., Target-mediated pharmacokinetic and pharmacodynamic model of exendin-4 in rats, monkeys, and humans. *Drug Metab. Dispos.* 40, 990-7, (2012).
Gellman, S.H. Foldamers: A Manifesto. *Acc. Chem. Res.* 31, 173-80, (1998).
Ghadiri et al., Secondary structure nucleation in peptides. Transition metal ion stabilized α-helices. *J. Am. Chem. Soc.* 112, 1630-32, (1990).
Goodman et al., Foldamers as versatile frameworks for the design and evolution of function. *Nat. Chem. Biol.* 3, 252-62 (2007).
Guichard et al., Synthetic foldamers. *Chem. Comm.* 47, 5933-41, (2011).
Handbook of Pharmaceutical Salts, P.H. Stahl and C.G. Wermuch, Eds., © 2002, Verlag Helvitica Chemica Acta (Surich, Switzerland (Book—Copy not provided).
Hansen et al., Glucagon-like peptide-1-(7-36)amide is transformed to glucagon-like peptide-1-(9-36)amide by dipeptidyl peptidase IV in the capillaries supplying the L cells of the porcine intestine. *Endocrinology* 140, 5356-63, (1999).
Horne et al., Foldamers with heterogeneous backbones. *Acc. Chem. Res.* 41, 1399-408 (2008).
Horne et al., Sequence-Based Design of α/β-Peptide Foldamers that Mimic ∀-Helical BH3 Domains, *Angew. Chem. Int. Ed.* 47, 2853-6, (2008).
Horne et al., Interplay among side chain sequence, backbone composition, and residue rigidification in polypeptide folding and assembly. *Proc. Natl Acad Sci USA* 105, 9151-6, (2008).
Horne et al., Structural and biological mimicry of protein surface recognition by α/β-peptide foldamers. *Proc. Natl. Acad. Sci. USA* 106, 14751-6, (2009).
Hupe-Sodmann et al., Characterisation of the processing by human neutral endopeptidase 24.11 of GLP-1(7-36) amide and comparison of the substrate specificity of the enzyme for other glucagon-like peptides. *Regul. Pept.* 58, 149-56, (1995).
Jackson et al., General approach to the synthesis of short α-helical peptides. *J. Am. Chem. Soc.* 113, 9391-2, (1991).
Jessen et al., Suppression of food intake by glucagon-like peptide-1 receptor agonists: relative potencies and role of dipeptidyl peptidase-4. *Endocrinology* 153, 5735-45, (2012).
Johnson et al., Enhancement of α-Helix Mimicry by an α/β-Peptide Foldamer via Incorporation of a Dense Ionic Side-Chain Array. *J. Am. Chem. Soc.* 134, 7317-20, (2012).
Johnson et al., α-Helix Mimicry with α/β-Peptides, *Meth. Enzymol.* 523, 407-29, (2013).
Johnson, Lisa M., "Development of α/β Peptides as Fusion Inhibitors of HIV and Agonists of Glucagon-Like Peptide-1 Receptor (GLP-1R)," Dissertation, Aug. 30, 2012, 254 pgs., University of Wisconsin—Madison, Madison, WI.
Judice et al., Inhibition of HIV type 1 infectivity by constrained α-helical peptides: implications for the viral fusion mechanism. *Proc. Natl. Acad. Sci. USA* 94, 13426-30, (1997).
Lagerstrom et al., Structural diversity of G protein-coupled receptors and significance for drug discovery. *Nature Reviews. Drug Discovery* 7, 339-57, (2008).
Miranda et al., Design and synthesis of conformationally constrained glucagon-like peptide-1 derivatives with increased plasma stability and prolonged in vivo activity. *J. Med. Chem.* 51, 2758-65, (2008).
Murage et al., Development of Potent Glucagon-like Peptide-1 Agonists with High Enzyme Stability via Introduction of Multiple Lactam Bridges. *J. Med. Chem.* 53, 6412-20, (2010).
Okamoto et al., Stabilization the pro-apoptotic BimBH3 helix (BimSAHB) does not necessarily enhance affinity of biological activity. *ACS Chem. Biol.* 8, 297-302, (2013).
Parkes et al., Pharmacokinetic actions of exendin-4 in the rat: Comparison with glucagon-like peptide-1, *Drug Dev. Res.* 53, 260-7, (2001).
Phillips et al., Design and structure of stapled peptides binding to estrogen receptors, *J. Am. Chem. Soc.* 133, 9696-9, (2011).
Price et al., Detection and Analysis of Chimeric Tertiary Structure via Backbone Thioester Exchange: Packing of an α-Helix against an α/β-Peptide Helix, *Angew. Chem. Int. Ed.* 49, 368-71, (2010).
Rabaglia et al., Alpha-Ketoisocaproate-induced hypersecretion of insulin by islets from diabetes-susceptible mice. *Am. J. Physiol. Endocrinol. Metab.* 289, E218-24, (2005).
RCSB Protein Bata Bank Entry 1DOR, Solution Structure of Glucagon-Like Peptide 1-(7-36)-Amide in Trifluorethanol/water, Jul. 12, 2016.
Ridge et al., Comparison of Safety and Tolerability With Continuous (Exenatide Once Weekly) or Intermittent (Exenatide Twice Daily) Glp-1 Receptor Agonism in Patients With Type 2 Diabetes. *Diabetes Obes. Metab.* 14, 1097-1103, (2012).
Salomon et al.,A highly sensitive adenylate cyclase assay. *Anal. Biochem.* 58, 541-8, (1974).
Stewart et al., The Mcl-1 BH3 helix is an exclusive Mcl-1 inhibitor and apoptosis sensitizer, *Nat. Chem. Biol.* 6, 595-601, (2010).
Thermo Scientific "Thermo Scientific Pierce Antibody Production and Purification Technical Handbook" Published 2010.
Trivedi et al., Design and synthesis of conformationally constrained glucagon analogues. *J. Med. Chem.* 43, 1714-22, (2000).
Underwood et al., Crystal Structure of Glucagon-like Peptide-1 in Complex with the Extracellular Domain of the Glucagon-like Peptide-1 Receptor. *J. Biol. Chem.* 285, 723-30, (2010).
Verdine et al., Stapled peptides for intracellular drug targets. *Meth. Enzymol.* 503, 3-33, (2012).
Walensky et al., Activation of apoptosis in vivo by a hydrocarbon-stapled BH3 helix. *Science* 305, 1466-70, (2004).
Yin et al., Strategies of targeting protein-protein interactions with synthetic agents. *Angew. Chem. Int. Ed.* 44, 4130-63, (2005).

* cited by examiner

GLP-1(7-37)-$NH_2$:

H-HAEGTFTSDVSSYLEGQAAKEFIAWLVKGRG-$NH_2$ (SEQ. ID. NO: 1)

H-HAEGTFTSDVSSYLEGQAAKEFIAWLVKGRG-$NH_2$ (SEQ. ID. NO: 2)

H-HAEGTFTSDVSSYLEGQAAXEFIXWLVZGRG-$NH_2$ (SEQ. ID. NO: 3)

H-HAEGTFTSDVSSYLEXQAAXEFIXWLVZGRG-$NH_2$ (SEQ. ID. NO: 4)

H-HAEGTFTSDVSXYLEXQAAXEFIXWLVZGRG-$NH_2$ (SEQ. ID. NO: 5)

H-HAEGTFTXDVSXYLEXQAAXEFIXWLVZGRG-$NH_2$ (SEQ. ID. NO: 6)

H-HAEGTFTSDASXYLEXQAAXEFIXWLVZGRG-$NH_2$ (SEQ. ID. NO: 7)

H-HAEGTFTSDASSYLEGQAAKEFIAWLVKGRG-$NH_2$ (SEQ. ID. NO: 8)

H-HAEGTFTSDASAYLEAQAAAEFIAWLVAGRG-$NH_2$ (SEQ. ID. NO: 9)

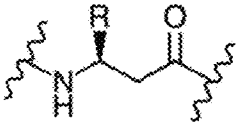

$\beta^3$ (double underline)

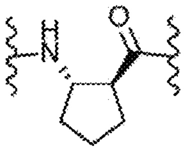

X = ACPC

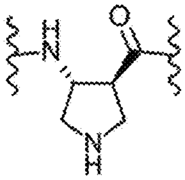

Z = APC

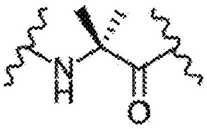

A = Aib

FIG. 1

H-HAEGTF//TSDVSSY//LEGQAAKEF//IAWLVKGRG-NH2 (SEQ. ID. NO: 1)

H-HAEGTF//TSDASXYLEXQAAXEFIXWLVZGRG-$NH_2$ (SEQ. ID. NO: 7)

H-HAEGTF//TSDASAY//LEAQAAAEF//IAWLVAGRG-$NH_2$ (SEQ. ID. NO: 9)

H-HAEGTF//TSDV//SSY//LEGQAA//KEF//IAWLVKGRG-$NH_2$ (SEQ. ID. NO: 1)

H-HAEGT//F//T//SDASXY//LEXQAAXEFIXWLVZGRG-$NH_2$ (SEQ. ID. NO: 7)

H-HAEGT//F//T//SDASAY//L//EAQAAAEF//IAWLVAGRG-$NH_2$ (SEQ. ID. NO: 9)

H-HA//EGTFTSDVSSYLEGQAAKEFIAWLVKGRG-$NH_2$ (SEQ. ID. NO: 1)

SEQUENCE LISTING

```
<160> NUMBER OF SEQ ID NOS: 16

<210> SEQ ID NO 1
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Human glucagon-like peptide 1, GLP-1-(7-37).

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30


<210> SEQ ID NO 2
<211> LENGTH: 31
<212> TYPE: PRT
<213> ORGANISM: Artificial Sequence
<220> FEATURE:
<223> OTHER INFORMATION: Non-natural alpha-beta polypeptide
<220> FEATURE:
<221> NAME/KEY: MOD_RES
<222> LOCATION: (20)..(20)
<223> OTHER INFORMATION: "X" at position 20 is beta3-lysine.
<220> FEATURE:
<221> NAME/KEY: MOD_RES
<222> LOCATION: (24)..(24)
<223> OTHER INFORMATION: "X" at position 24 is beta3-alanine.
```

```
<220> FEATURE:
<221> NAME/KEY: MOD_RES
<222> LOCATION: (28)..(28)
<223> OTHER INFORMATION: "X" at position 28 is beta3-lysine.

<400> SEQUENCE: 2

His Ala Glu Gly Thr Phe Thr Ser Asp Val Ser Ser Tyr Leu Glu Gly
1               5                   10                  15

Gln Ala Ala Xaa Glu Phe Ile Xaa Trp Leu Val Xaa Gly Arg Gly
            20                  25                  30


<210> SEQ ID NO 3
<211> LENGTH: 31
<212> TYPE: PRT
<213> ORGANISM: Artificial Sequence
<220> FEATURE:
<223> OTHER INFORMATION: Non-natural alpha-beta polypeptide
<220> FEATURE:
<221> NAME/KEY: MOD_RES
<222> LOCATION: (20)..(20)
<223> OTHER INFORMATION: "X" at position 20 is 2-aminocyclopentane
      carboxylic acid
<220> FEATURE:
<221> NAME/KEY: MOD_RES
<222> LOCATION: (24)..(24)
<223> OTHER INFORMATION: "X" at position 24 is 2-aminocyclopentane
      carboxylic acid
<220> FEATURE:
<221> NAME/KEY: MOD_RES
<222> LOCATION: (28)..(28)
<223> OTHER INFORMATION: "X" at position 28 is 2-aminopyrrolidine-4-
      carboxylic acid

<400> SEQUENCE: 3

His Ala Glu Gly Thr Phe Thr Ser Asp Val Ser Ser Tyr Leu Glu Gly
1               5                   10                  15

Gln Ala Ala Xaa Glu Phe Ile Xaa Trp Leu Val Xaa Gly Arg Gly
            20                  25                  30


<210> SEQ ID NO 4
<211> LENGTH: 31
<212> TYPE: PRT
<213> ORGANISM: Artificial Sequence
<220> FEATURE:
<223> OTHER INFORMATION: Non-natural alpha-beta polypeptide
<220> FEATURE:
<221> NAME/KEY: MOD_RES
<222> LOCATION: (16)..(16)
<223> OTHER INFORMATION: "X" at position 16 is 2-aminocyclopentane
      carboxylic acid
<220> FEATURE:
<221> NAME/KEY: MOD_RES
<222> LOCATION: (20)..(20)
<223> OTHER INFORMATION: "X" at position 20 is 2-aminocyclopentane
      carboxylic acid
<220> FEATURE:
<221> NAME/KEY: MOD_RES
<222> LOCATION: (24)..(24)
<223> OTHER INFORMATION: "X" at position 24 is 2-aminocyclopentane
      carboxylic acid
<220> FEATURE:
<221> NAME/KEY: MOD_RES
<222> LOCATION: (28)..(28)
<223> OTHER INFORMATION: "X" at position 24 is 2-aminopyrrolidine-4-
      carboxylic acid

<400> SEQUENCE: 4

His Ala Glu Gly Thr Phe Thr Ser Asp Val Ser Ser Tyr Leu Glu Xaa
1               5                   10                  15

Gln Ala Ala Xaa Glu Phe Ile Xaa Trp Leu Val Xaa Gly Arg Gly
            20                  25                  30
```

-continued

<210> SEQ ID NO 5
<211> LENGTH: 31
<212> TYPE: PRT
<213> ORGANISM: Artificial Sequence
<220> FEATURE:
<223> OTHER INFORMATION: Non-natural alpha-beta polypeptide
<220> FEATURE:
<221> NAME/KEY: MOD_RES
<222> LOCATION: (12)..(12)
<223> OTHER INFORMATION: "X" at position 12 is 2-aminocyclopentane carboxylic acid
<220> FEATURE:
<221> NAME/KEY: MOD_RES
<222> LOCATION: (16)..(16)
<223> OTHER INFORMATION: "X" at position 16 is 2-aminocyclopentane carboxylic acid
<220> FEATURE:
<221> NAME/KEY: MOD_RES
<222> LOCATION: (20)..(20)
<223> OTHER INFORMATION: "X" at position 20 is 2-aminocyclopentane carboxylic acid
<220> FEATURE:
<221> NAME/KEY: MOD_RES
<222> LOCATION: (24)..(24)
<223> OTHER INFORMATION: "X" at position 24 is 2-aminocyclopentane carboxylic acid
<220> FEATURE:
<221> NAME/KEY: MOD_RES
<222> LOCATION: (28)..(28)
<223> OTHER INFORMATION: "X" at position 24 is 2-aminopyrrolidine-4-carboxylic acid

<400> SEQUENCE: 5

```
His Ala Glu Gly Thr Phe Thr Ser Asp Val Ser Xaa Tyr Leu Glu Xaa
1               5                   10                  15

Gln Ala Ala Xaa Glu Phe Ile Xaa Trp Leu Val Xaa Gly Arg Gly
            20                  25                  30
```

<210> SEQ ID NO 6
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: "X" at position 8 is 2-aminocyclopentane carboxylic acid
<220> FEATURE:
<221> NAME/KEY: MOD_RES
<222> LOCATION: (12)..(12)
<223> OTHER INFORMATION: "X" at position 12 is 2-aminocyclopentane carboxylic acid
<220> FEATURE:
<221> NAME/KEY: MOD_RES
<222> LOCATION: (16)..(16)
<223> OTHER INFORMATION: "X" at position 16 is 2-aminocyclopentane carboxylic acid
<220> FEATURE:
<221> NAME/KEY: MOD_RES
<222> LOCATION: (20)..(20)
<223> OTHER INFORMATION: "X" at position 20 is 2-aminocyclopentane carboxylic acid
<220> FEATURE:
<221> NAME/KEY: MOD_RES
<222> LOCATION: (24)..(24)
<223> OTHER INFORMATION: "X" at position 24 is 2-aminocyclopentane carboxylic acid
<220> FEATURE:
<221> NAME/KEY: MOD_RES
<222> LOCATION: (28)..(28)
<223> OTHER INFORMATION: "X" at position 28 is 2-aminopyrrolidine-4-carboxylic acid -continued

<400> SEQUENCE: 6

His Ala Glu Gly Thr Phe Thr Xaa Asp Val Ser Xaa Tyr Leu Glu Xaa
1 5 10 15

Gln Ala Ala Xaa Glu Phe Ile Xaa Trp Leu Val Xaa Gly Arg Gly
20 25 30

<210> SEQ ID NO 7
<211> LENGTH: 31
<212> TYPE: PRT
<213> ORGANISM: Artificial Sequence
<220> FEATURE:
<223> OTHER INFORMATION: Non-natural alpha-beta polypeptide
<220> FEATURE:
<221> NAME/KEY: MOD_RES
<222> LOCATION: (2)..(2)
<223> OTHER INFORMATION: "X" at position 2 is 2-aminoisobutyric acid (i.e., 2-methylalanine).
<220> FEATURE:
<221> NAME/KEY: MOD_RES
<222> LOCATION: (10)..(10)
<223> OTHER INFORMATION: "X" at position 10 is 2-aminoisobutyric acid (i.e., 2-methylalanine).
<220> FEATURE:
<221> NAME/KEY: MOD_RES
<222> LOCATION: (12)..(12)
<223> OTHER INFORMATION: "X" at position 12 is 2-aminocyclopentane carboxylic acid
<220> FEATURE:
<221> NAME/KEY: MOD_RES
<222> LOCATION: (16)..(16)
<223> OTHER INFORMATION: "X" at position 16 is 2-aminocyclopentane carboxylic acid
<220> FEATURE:
<221> NAME/KEY: MOD_RES
<222> LOCATION: (20)..(20)
<223> OTHER INFORMATION: "X" at position 20 is 2-aminocyclopentane carboxylic acid
<220> FEATURE:
<221> NAME/KEY: MOD_RES
<222> LOCATION: (24)..(24)
<223> OTHER INFORMATION: "X" at position 24 is 2-aminocyclopentane carboxylic acid
<220> FEATURE:
<221> NAME/KEY: MOD_RES
<222> LOCATION: (28)..(28)
<223> OTHER INFORMATION: "X" at position 28 is 2-aminopyrrolidine-4-carboxylic acid

<400> SEQUENCE: 7

His Xaa Glu Gly Thr Phe Thr Ser Asp Xaa Ser Xaa Tyr Leu Glu Xaa
1 5 10 15

Gln Ala Ala Xaa Glu Phe Ile Xaa Trp Leu Val Xaa Gly Arg Gly
20 25 30

<210> SEQ ID NO 8
<211> LENGTH: 31
<212> TYPE: PRT
<213> ORGANISM: Artificial Sequence
<220> FEATURE:
<223> OTHER INFORMATION: Non-natural alpha-beta polypeptide
<220> FEATURE:
<221> NAME/KEY: MOD_RES
<222> LOCATION: (10)..(10)
<223> OTHER INFORMATION: "X" at position 10 is 2-aminoisobutyric acid (i.e., 2-methylalanine).

<400> SEQUENCE: 8

His Ala Glu Gly Thr Phe Thr Ser Asp Xaa Ser Ser Tyr Leu Glu Gly
1 5 10 15

Gln Ala Ala Lys Glu Phe Ile Ala Trp Leu Val Lys Gly Arg Gly
20 25 30

<210> SEQ ID NO 9
<211> LENGTH: 31
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: "X" at position 2 is 2-aminoisobutyric acid (i.e., 2-methylalanine).
<220> FEATURE:
<221> NAME/KEY: MOD_RES
<222> LOCATION: (10)..(10)
<223> OTHER INFORMATION: "X" at position 10 is 2-aminoisobutyric acid (i.e., 2-methylalanine).
<220> FEATURE:
<221> NAME/KEY: MOD_RES
<222> LOCATION: (12)..(12)
<223> OTHER INFORMATION: "X" at position 12 is 2-aminoisobutyric acid (i.e., 2-methylalanine).
<220> FEATURE:
<221> NAME/KEY: MOD_RES
<222> LOCATION: (16)..(16)
<223> OTHER INFORMATION: "X" at position 16 is 2-aminoisobutyric acid (i.e., 2-methylalanine).
<220> FEATURE:
<221> NAME/KEY: MOD_RES
<222> LOCATION: (20)..(20)
<223> OTHER INFORMATION: "X" at position 20 is 2-aminoisobutyric acid (i.e., 2-methylalanine).
<220> FEATURE:
<221> NAME/KEY: MOD_RES
<222> LOCATION: (24)..(24)
<223> OTHER INFORMATION: "X" at position 24 is 2-aminoisobutyric acid (i.e., 2-methylalanine).
<220> FEATURE:
<221> NAME/KEY: MOD_RES
<222> LOCATION: (28)..(28)
<223> OTHER INFORMATION: "X" at position 28 is 2-aminoisobutyric acid (i.e., 2-methylalanine).

<400> SEQUENCE: 9

```
His Xaa Glu Gly Thr Phe Thr Ser Asp Xaa Ser Xaa Tyr Leu Glu Xaa
1               5                   10                  15

Gln Ala Ala Xaa Glu Phe Ile Xaa Trp Leu Val Xaa Gly Arg Gly
            20                  25                  30
```

<210> SEQ ID NO 10
<211> LENGTH: 31
<212> TYPE: PRT
<213> ORGANISM: Homo sapiens

<400> SEQUENCE: 10

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

<210> SEQ ID NO 11
<211> LENGTH: 31
<212> TYPE: PRT
<213> ORGANISM: Artificial Sequence
<220> FEATURE:
<223> OTHER INFORMATION: Non-natural alpha-beta polypeptide
<220> FEATURE:
<221> NAME/KEY: MOD_RES
<222> LOCATION: (16)..(16)
<223> OTHER INFORMATION: "X" at position 16 is beta3-glycine
<220> FEATURE:
<221> NAME/KEY: MOD_RES
<222> LOCATION: (20)..(20)
<223> OTHER INFORMATION: "X" at position 20 is beta3-lysine

```
<220> FEATURE:
<221> NAME/KEY: MOD_RES
<222> LOCATION: (24)..(24)
<223> OTHER INFORMATION: "X" at position 24 is beta3-alanine
<220> FEATURE:
<221> NAME/KEY: MOD_RES
<222> LOCATION: (28)..(28)
<223> OTHER INFORMATION: "X" at position 28 is beta3-lysine

<400> SEQUENCE: 11

His Ala Glu Gly Thr Phe Thr Ser Asp Val Ser Ser Tyr Leu Glu Xaa
1               5                   10                  15

Gln Ala Ala Xaa Glu Phe Ile Xaa Trp Leu Val Xaa Gly Arg Gly
            20                  25                  30


<210> SEQ ID NO 12
<211> LENGTH: 31
<212> TYPE: PRT
<213> ORGANISM: Artificial Sequence
<220> FEATURE:
<223> OTHER INFORMATION: Non-natural alpha-beta polypeptide
<220> FEATURE:
<221> NAME/KEY: MOD_RES
<222> LOCATION: (12)..(12)
<223> OTHER INFORMATION: "X" at position 12 is beta3-serine
<220> FEATURE:
<221> NAME/KEY: MOD_RES
<222> LOCATION: (16)..(16)
<223> OTHER INFORMATION: "X" at position 16 is beta3-glycine
<220> FEATURE:
<221> NAME/KEY: MOD_RES
<222> LOCATION: (20)..(20)
<223> OTHER INFORMATION: "X" at position 20 is beta3-lysine
<220> FEATURE:
<221> NAME/KEY: MOD_RES
<222> LOCATION: (24)..(24)
<223> OTHER INFORMATION: "X" at position 24 is beta3-alanine
<220> FEATURE:
<221> NAME/KEY: MOD_RES
<222> LOCATION: (28)..(28)
<223> OTHER INFORMATION: "X" at position 28 is beta3-lysine

<400> SEQUENCE: 12

His Ala Glu Gly Thr Phe Thr Ser Asp Val Ser Xaa Tyr Leu Glu Xaa
1               5                   10                  15

Gln Ala Ala Xaa Glu Phe Ile Xaa Trp Leu Val Xaa Gly Arg Gly
            20                  25                  30


<210> SEQ ID NO 13
<211> LENGTH: 31
<212> TYPE: PRT
<213> ORGANISM: Artificial Sequence
<220> FEATURE:
<223> OTHER INFORMATION: Non-natural alpha-beta polypeptide
<220> FEATURE:
<221> NAME/KEY: MOD_RES
<222> LOCATION: (2)..(2)
<223> OTHER INFORMATION: "X" at position 2 is 2-aminoisobutyric acid
      (i.e., 2-methylalanine).
<220> FEATURE:
<221> NAME/KEY: MOD_RES
<222> LOCATION: (10)..(10)
<223> OTHER INFORMATION: "X" at position 10 is 2-aminoisobutyric acid
      (i.e., 2-methylalanine).
<220> FEATURE:
<221> NAME/KEY: MOD_RES
<222> LOCATION: (12)..(12)
<223> OTHER INFORMATION: "X" at position 12 is beta3-serine
<220> FEATURE:
<221> NAME/KEY: MOD_RES
<222> LOCATION: (16)..(16)
<223> OTHER INFORMATION: "X" at position 16 is beta3-glycine
```

<220> FEATURE:
<221> NAME/KEY: MOD_RES
<222> LOCATION: (20)..(20)
<223> OTHER INFORMATION: "X" at position 20 is beta3-lysine
<220> FEATURE:
<221> NAME/KEY: MOD_RES
<222> LOCATION: (24)..(24)
<223> OTHER INFORMATION: "X" at position 24 is beta3-alanine
<220> FEATURE:
<221> NAME/KEY: MOD_RES
<222> LOCATION: (28)..(28)
<223> OTHER INFORMATION: "X" at position 24 is beta3-lysine

<400> SEQUENCE: 13

His Xaa Glu Gly Thr Phe Thr Ser Asp Xaa Ser Xaa Tyr Leu Glu Xaa
1 5 10 15

Gln Ala Ala Xaa Glu Phe Ile Xaa Trp Leu Val Xaa Gly Arg Gly
20 25 30

<210> SEQ ID NO 14
<211> LENGTH: 31
<212> TYPE: PRT
<213> ORGANISM: Artificial Sequence
<220> FEATURE:
<223> OTHER INFORMATION: Non-natural alpha-beta polypeptide
<220> FEATURE:
<221> NAME/KEY: MOD_RES
<222> LOCATION: (10)..(10)
<223> OTHER INFORMATION: "X" at position 10 is 2-aminoisobutyric acid (i.e., 2-methylalanine).

<400> SEQUENCE: 14

His Ala Glu Gly Thr Phe Thr Ser Asp Xaa Ser Ser Tyr Leu Glu Gly
1 5 10 15

Gln Ala Ala Lys Glu Phe Ile Ala Trp Leu Val Lys Gly Arg Gly
20 25 30

<210> SEQ ID NO 15
<211> LENGTH: 32
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: "X" at position 20 is is a beta2- or beta3-amino acid. It may be unsubstituted, substituted at the beta2-and/or beta3-position backbone carbon atoms, The beta2- and/or beta3-position backbone carbon atoms may be incorporated into a 4-to 8-member ring.
<220> FEATURE:
<221> NAME/KEY: MOD_RES
<222> LOCATION: (25)..(25)
<223> OTHER INFORMATION: "X" at position 25 is is a beta2- or beta3-amino acid. It may be unsubstituted, substituted at the beta2-and/or beta3-position backbone carbon atoms, The beta2- and/or beta3-position backbone carbon atoms may be incorporated into a 4-to 8-member ring.
<220> FEATURE:
<221> NAME/KEY: MOD_RES
<222> LOCATION: (29)..(29)
<223> OTHER INFORMATION: "X" at position 29 is is a beta2- or beta3-amino acid. It may be unsubstituted, substituted at the beta2-and/or beta3-position backbone carbon atoms, The beta2- and/or beta3-position backbone carbon atoms may be incorporated into a 4-to 8-member ring.

<400> SEQUENCE: 15

His Ala Glu Gly Thr Phe Thr Ser Asp Val Ser Ser Tyr Leu Glu Gly
1 5 10 15

Gln Ala Ala Xaa Lys Glu Phe Ile Xaa Trp Leu Val Xaa Gly Arg Gly
20 25 30

-continued

```
<210> SEQ ID NO 16
<211> LENGTH: 32
<212> TYPE: PRT
<213> ORGANISM: Artificial Sequence
<220> FEATURE:
<223> OTHER INFORMATION: Synthetic, unnatural polypeptide..
<220> FEATURE:
<221> NAME/KEY: MISC_FEATURE
<222> LOCATION: (3)..(3)
<223> OTHER INFORMATION: "X" at position 3 is Ala or 2-aminoisobutyric
      acid ("Aib").
<220> FEATURE:
<221> NAME/KEY: MISC_FEATURE
<222> LOCATION: (9)..(9)
<223> OTHER INFORMATION: "X" at position 9 is Ser or 2-aminocyclopentane
      carboxylic acid ("ACPC").
<220> FEATURE:
<221> NAME/KEY: MISC_FEATURE
<222> LOCATION: (11)..(11)
<223> OTHER INFORMATION: "X" at position 11 is Val or Aib.
<220> FEATURE:
<221> NAME/KEY: MISC_FEATURE
<222> LOCATION: (13)..(13)
<223> OTHER INFORMATION: "X" at position 13 is Ser, beta3-Ser, Aib, or
      ACPC.
<220> FEATURE:
<221> NAME/KEY: MISC_FEATURE
<222> LOCATION: (17)..(17)
<223> OTHER INFORMATION: "X" at position 17 is Gly, beta3-Gly, Aib, or
      ACPC.
<220> FEATURE:
<221> NAME/KEY: MISC_FEATURE
<222> LOCATION: (21)..(21)
<223> OTHER INFORMATION: "X" at position 21 is beta3-Lys, Aib, or ACPC.
<220> FEATURE:
<221> NAME/KEY: MISC_FEATURE
<222> LOCATION: (25)..(25)
<223> OTHER INFORMATION: "X" at position 25 is Ala, Aib, or ACPC.
<220> FEATURE:
<221> NAME/KEY: MISC_FEATURE
<222> LOCATION: (29)..(29)
<223> OTHER INFORMATION: "X" at position 29 is Lys, beta3-Lys, Aib, or
      3-aminopyrrolidine-4-carboxylic acid.

<400> SEQUENCE: 16

His His Xaa Glu Gly Thr Phe Thr Xaa Asp Xaa Ser Xaa Tyr Leu Glu
1               5                   10                  15

Xaa Gln Ala Ala Xaa Glu Phe Ile Xaa Trp Leu Val Xaa Gly Arg Gly
            20                  25                  30
```

ALPHA/BETA-POLYPEPTIDE ANALOGS OF GLUCAGON-LIKE PEPTIDE 1

CROSS-REFERENCE TO RELATED APPLICATIONS

This is a divisional of co-pending application Ser. No. 14/312,081, filed Jun. 23, 2014, which claims priority to provisional application Ser. No. 61/838,300, filed Jun. 23, 2013, both of which are incorporated herein by reference.

FEDERAL FUNDING STATEMENT

This invention was made with government support under GM056414 awarded by the National Institutes of Health. The government has certain rights in the invention.

BACKGROUND

Despite insulin being available as an injectable treatment for diabetes mellitus since the 1920's, diabetes continues to be a chronic public health issue. Thus, intense research continues to find alternative treatments for diabetes and related metabolic disorders. In recent years, considerable research effort has been focused on incorporating glucagon-like peptide-1 (GLP-1) into a viable treatment for diabetes. GLP-1 is secreted by ileal L cells. Secretion is dependent upon the presence of nutrients in the lumen of the small intestine. GLP-1 is a potent anti-hyperglycemic hormone. Additionally, GLP-1 is known to inhibit pancreatic β-cell apoptosis and stimulate the proliferation and differentiation of insulin-secreting β-cells. It is secreted as a pro-protein, which is then post-translationally modified to yield two physiologically active forms: GLP-1(7-37) and GLP-1(7-36)-$NH_2$.

GLP-1(7-36)-$NH_2$ is a polypeptide having 30 amino acid residues (residues 7-36 of the proglucagon precursor), with a primary amide ($NH_2$) bonded to the carboxy terminus. GLP-1(7-37) is a polypeptide having 31 amino acid residues (residues 7-37 of the proglucagon precursor). Both versions have the same insulinotropic hormone secretion action. For a discussion of GLP-1 and the functionally related insulinotropic hormones extendin-3 and extendin-4, see U.S. Pat. No. 5,424,286, issued Jun. 13, 1995 to John Eng.

GLP-1 is the natural agonist for GLP-1R, a G protein-coupled receptor (GPCR) that is displayed on the surface of pancreatic β cells. Activation of GLP-1R augments glucose-dependent insulin release from β cells and, as noted above, promotes β cell survival. These properties are attractive for treatment of type 2 diabetes. However, GLP-1 is rapidly degraded by peptidases in vivo. Its half-life in vivo is less than two (2) minutes. Efforts to develop small-molecule agonists of GLP-1R have not been successful, presumably because receptor activation requires contact over an extended surface. All non-natural GLP-1R agonists reported to date consist exclusively of α-amino acid residues. In the non-natural GLP-1R agonists now known, in vivo activity is prolonged via several approaches, such as varying the sequence of α-amino acid residues, incorporating stabilizing appendages, and/or utilizing specialized delivery strategies. GLP-1 derivatives have been approved for sale for use in humans in the United States. See, for example, Victoza®-brand liraglutide (rDNA origin) for injection, marketed commercially by Novo Nordisk, Inc., Plainsboro, N.J. See also U.S. Pat. Nos. 6,268,343; 6,458,924; 7,235,627; and 8,114,833.

As used herein, the term "diabetes mellitus" or simply "diabetes" is used in a very broad sense to encompass metabolic disorders in which a subject has high blood sugar (i.e., hyperglycemia). Hyperglycemic conditions have various etiologies, such as because the pancreas does not produce enough insulin, or because cells do not respond to the insulin that is produced. There are several recognized subtypes of diabetes, some of which are better understood than others. Type 1 diabetes is characterized by the complete failure of the body to produce insulin or the failure of the body to produce enough insulin. Type 2 diabetes generally results from insulin resistance, a condition in which cells fail to use insulin properly. Type 2 diabetes sometimes co-presents with an insulin deficiency. Gestational diabetes occurs when pregnant women without a previous diagnosis of diabetes develop hyperglycemia. Less common forms of diabetes include congenital diabetes (due to genetic defects relating to insulin secretion), cystic fibrosis-related diabetes, steroid diabetes induced by high doses of glucocorticoids, and several forms of monogenic diabetes (also known as maturity onset diabetes of the young). These last two terms are catch-all phrases that refer to several hereditary forms of diabetes caused by mutations in a single, autosomal dominant gene (as contrasted to more complex, polygenic etiologies resulting in hyperglycemia).

SUMMARY OF THE INVENTION

Disclosed and claimed herein is an alternative approach for designing GLP-1R agonists. The agonists described herein retain GLP-1-like function but have prolonged activity in vivo. The present work includes strategically replacing native α-amino acid residues with conformationally constrained β-amino acid residues in GLP-1 and its pharmacologically active derivatives (e.g., native GLP-1-(7-37) and GLP-1-(7-36)-$NH_2$.) As shown in the examples, this approach yields potent GLP-1R agonists that are highly resistant to digestion by proteolytic enzymes.

Thus, disclosed herein is a composition of matter comprising a glucagon-like peptide 1 (GLP-1) having an N-terminus and comprised of α-amino acid residues, wherein at least one α-amino acid residue in the GLP-1 located at least 12 residues from the N-terminus of the GLP-1 is replaced with a β-amino acid residue. The at least one α-amino acid residue that is replaced may be replaced with a cyclically constrained β-amino acid residue.

Also disclosed herein is a composition of matter comprising a GLP-1 having an N-terminus and comprised of α-amino acid residues, wherein at least two α-amino acid residues in the GLP-1, each located at least 12 residues from the N-terminus of the GLP-1, is replaced with a β-amino acid residue. Again, the at least two α-amino acid residues may be replaced with cyclically constrained β-amino acid residues.

Further disclosed herein is a composition of matter comprising a GLP-1 having an N-terminus and comprised of α-amino acid residues, wherein at least three α-amino acid residues in the GLP-1, each located at least 12 residues from the N-terminus of the GLP-1, is replaced with a β-amino acid residue. The at least three α-amino acid residues may be replaced with cyclically constrained β-amino acid residues.

Also disclosed herein is a glucagon-like peptide-1 receptor agonist comprising a composition of matter as recited above, wherein the composition of matter retains at least 5%, at least 10%, at least 20%, at least 30%, and least 40%, and least 50%, at least 60%, at least 70%, at least 80%, or at least 90% of the agonist activity in vivo of native human GLP-1.

Additionally described is a glucagon-like peptide-1 receptor agonist comprising a composition of matter as recited above, wherein the composition of matter has an agonist activity half-life in vivo, in humans, greater than native human GLP-1.

Also described herein are polypeptides that are useful as glucagon-like peptide 1 receptor agonists. Thus, one set of the polypeptides are selected from the group consisting of H-HAEGTFTSDVSSYLEGQAA-X-KEFI-X-WLV-X-GRG-$NH_2$ (SEQ. ID. NO: 15), wherein each "X," which may be the same or different, is a β-amino acid residue. At least one "X" may be a β-amino acid residue whose α- and β-position carbon atoms are incorporated into a ring (i.e., a cyclically constrained β-amino residue). Each "X" may optionally and independently be selected from the group consisting of $\beta^3$-homo-alanine, $\beta^3$-homo-lysine, ACPC, and APC. Included within the group of polypeptides are SEQ. ID. NOS: 2-7 and 11-13.

Further disclosed herein is a method to stimulate a glucagon-like peptide-1 receptor in vitro. The method comprises contacting the receptor with a composition of matter as recited above, a glucagon-like peptide-1 receptor agonist as recited above, or a polypeptide as recited above.

Another embodiment described herein is a method to stimulate a glucagon-like peptide-1 receptor in vivo in a mammalian subject, including a human subject. The method comprising administering to the subject a glucagon-like peptide-1 receptor agonist-effective amount of a composition of matter as recited herein, a glucagon-like peptide-1 receptor agonist as recited herein, or a GLP-1 analog as described herein.

Also disclosed are pharmaceutical or nutritional compositions comprising a composition of matter as herein, a glucagon-like peptide-1 receptor agonist as recited herein, or a GLP-1 analog as recited herein, in combination with a pharmaceutically suitable carrier or other nutritionally significant ingredients.

Yet another aspect of the disclosure is a method to fabricate glucagon-like peptide-1 receptor agonists that are resistant to proteolytic degradation. The method comprises constructing a glucagon-like peptide 1 (GLP-1) analog having an amino acid sequence identical to a native GLP-1 sequence, but replacing at least one α-amino acid residue in the native GLP-1 sequence with a β-amino acid residue, wherein the replacement β-amino acid residue is located at least 12 residues from the N-terminus of the GLP-1 analog. The at least one α-amino acid residue may be replaced with a cyclically constrained β-amino acid residue. More than one α-amino acid residue may be replaced with a β-amino acid residue, and each replacement is independent of the other replacements. For example, at least two or at least three α-amino acid residues in the native GLP-1 may be replaced with β-amino acid residues. Each replacement β-amino acid residue is located at least 12 residues from the N-terminus of the GLP-1.

Also disclosed herein is a method to treat hyperglycemia and diabetes in a mammalian subject, including a human subject. The method comprising administering to the subject a anti-hyperglycemic-effective amount of a composition of matter as recited herein, a glucagon-like peptide-1 receptor agonist as recited herein, a GLP-1 analog as recited herein, or a pharmaceutical composition as herein.

BRIEF DESCRIPTION OF THE DRAWINGS

FIG. 1: Sequences of GLP-1(7-37)-$NH_2$ (SEQ. ID. NO: 1) and α/β-peptide analogs (SEQ. ID. NOS: 2-7). Each molecule has a free N-terminus and a primary amide at the C-terminus. The single-letter code is used to refer to proteinogenic α-amino acid residues. X=ACPC; Z=APC; A=the non-proteinogenic α residue Aib; double underlined residues are $\beta^3$ homologs of proteingenic α residues.

SEQUENCE LIST

Figure 2:
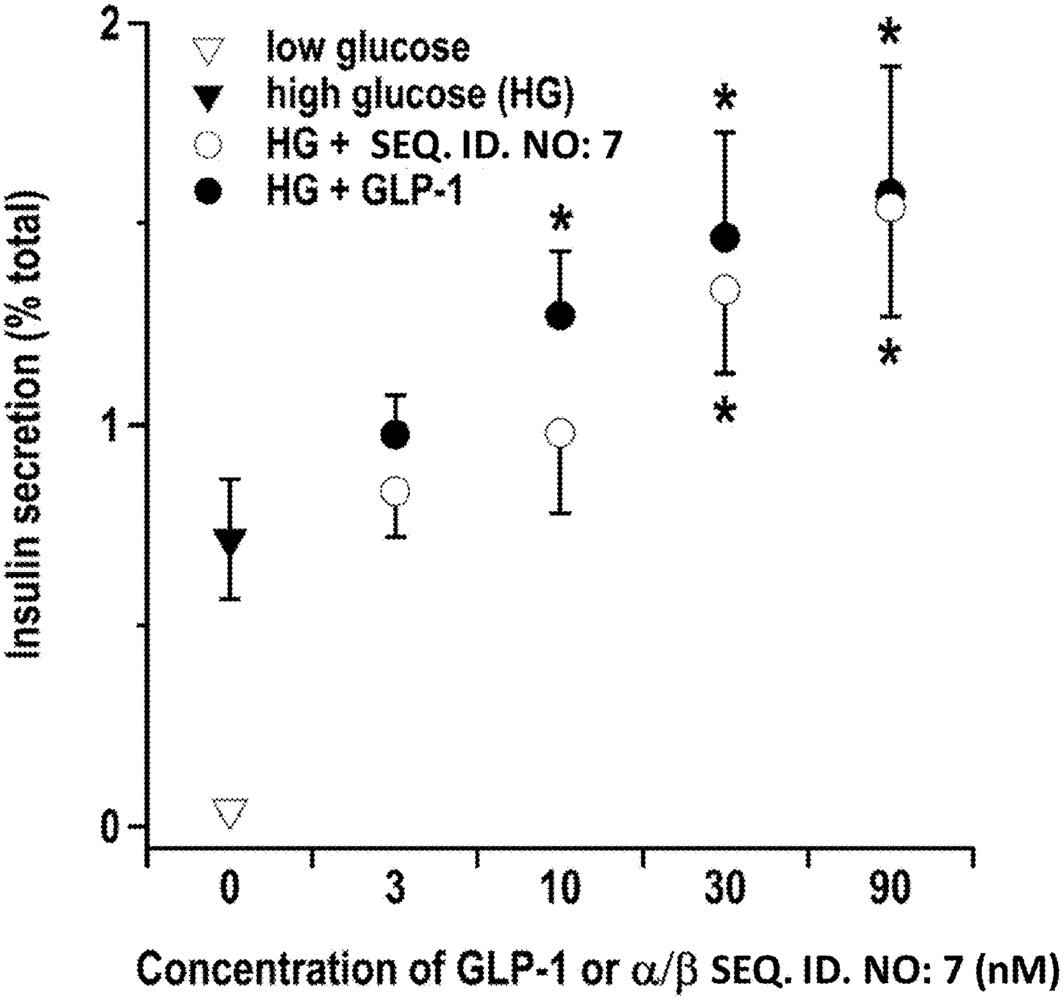
FIG. 2: α/β-Peptide SEQ. ID. NO: 7 and GLP-1 (SEQ. ID. NO: 1) are equally effective insulin segretagogues. Insulin secretion was monitored from primary mouse islets in response to low glucose alone (3 mM, ∇) or high glucose (HG, 16 mM) in the absence (▼) or presence of varying concentrations of the α/β-peptide SEQ. ID. NO: 7 (○) or GLP-1(7-36)-$NH_2$ SEQ. ID. NO: 1 (●). Measurements show the mean of five (5) independent experiments (±SEM). Secretion is plotted as the percentage of total insulin content per islet. *, $P<0.05$ for α/β-peptide (SEQ. ID. NO: 7) or GLP-1(7-36)-$NH_2$ (SEQ. ID. NO: 1) vs HG alone.

The following sequence identifiers are used throughout the description and claims:

(SEQ. ID. NO: 1)
H-HAEGTFTSDVSSYLEGQAAKEFIAWLVKGRG-$NH_2$ (SEQ. ID. NO: 2)
H-HAEGTFTSDVSSYLEGQAAKEFIAWLVKGRG-$NH_2$ (SEQ. ID. NO: 3)
H-HAEGTFTSDVSSYLEGQAAXEFIXWLVZGRG-$NH_2$ (SEQ. ID. NO: 4)
H-HAEGTFTSDVSSYLEXQAAXEFIXWLVZGRG-$NH_2$ (SEQ. ID. NO: 5)
H-HAEGTFTSDVSXYLEXQAAXEFIXWLVZGRG-$NH_2$ (SEQ. ID. NO: 6)
H-HAEGTFTXDVSXYLEXQAAXEFIXWLVZGRG-$NH_2$ (SEQ. ID. NO: 7)
H-HAEGTFTSDASXYLEXQAAXEFIXWLVZGRG-$NH_2$ (SEQ. ID. NO: 8)
H-HAEGTFTSDASSYLEGQAAKEFIAWLVKGRG-$NH_2$ (SEQ. ID. NO: 9)
H-HAEGTFTSDASAYLEAQAAAEFIAWLVAGRG-$NH_2$

Key for SEQ. ID. NOS: 1-9

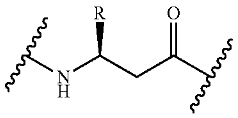

$\underline{\underline{B}}^3$ (double underline)

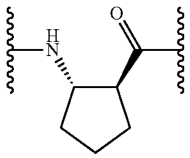

X = ACPC

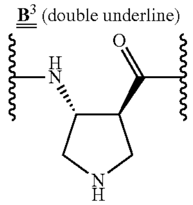

Z = APC

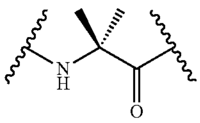

$\underline{A}$ = Aib (SEQ. ID. NO: 10)
H-HAEGTFTSDVSSYLEGQAAKEFIAWLVKGRG-$NH_2$ (SEQ. ID. NO: 11)
H-HAEGTFTSDVSSYLEGQAAKEFIAWLVKGRG-$NH_2$ (SEQ. ID. NO: 12)
H-HAEGTFTSDVSSYLEGQAAKEFIAWLVKGRG-$NH_2$ (SEQ. ID. NO: 13)
H-HAEGTFTSDASSYLEGQAAKEFIAWLVKGRG-$NH_2$ (SEQ. ID. NO: 14)
H-HAEGTFTSDASSYLEGQAAKEFIAWLVKGRG-$NH_2$ Key for SEQ. ID. NOS: 10-14:

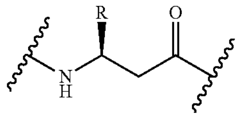

double underlined residues

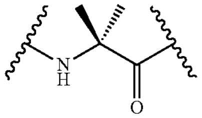

$\underline{A}$

H-HAEGTFTSDVSSYLEGQAA-X-KEFI-X-WLV-X-GRG-$NH_2$ (SEQ. ID. NO: 15), wherein each "X," which may be the same or different, is a β-amino acid residue. The β-amino acid residue may be unsubstituted, substituted at the α- and/or β-position backbone carbon atoms, or the α- and/or β-position backbone carbon atoms may be incorporated into a C4 to C8 ring (carbonaceous or hetercyclic, saturated or containing one or more unsaturations).

H-H-X-EGTFT-X-D-X-S-X-YLE-X-QAA-X-EFI-X-WLV-X-GRG-$NH_2$ (SEQ. ID. NO: 16), wherein:

X at position 3 is Ala or 2-aminoisobutyric acid ("Aib");

X at position 9 is Ser or 2-aminocyclopentane carboxylic acid ("ACPC");

X at position 11 is Val or Aib;

X at position 13 is Ser, $\beta^3$-Ser, Aib, or ACPC;

X at position 17 is Gly, $\beta^3$-Gly, Aib, or ACPC;

X at position 21 is $\beta^3$-Lys, Aib, or ACPC;

X at position 25 is Ala, Aib, or ACPC; and

X at position 29 is Lys, $\beta^3$-Lys, Aib, or 3-aminopyrrolidine-4-carboxylic acid.

DETAILED DESCRIPTION

Abbreviations and Definitions

ACPC=2-aminocyclopentane carboxylic acid.

Aib=2-aminoisobutyric acid (i.e., 2-methylalanine)

APC=3-aminopyrrolidine-4-carboxylic acid.

cAMP=cyclic adenosine monophosphate.

"Cyclically constrained" when referring to a β-amino acid or β-amino acid residue means a β-amino acid or β-amino acid residue in which the α-position and β-position carbon atoms in the backbone of the β-amino acid are incorporated into a substituted or unsubstituted $C_4$ to $C_{10}$ cycloalkyl, cycloalkenyl, or heterocycle moiety, wherein heterocycle moieties may have 1, 2, or 3 heteroatoms selected from the group consisting of N, S, and O. Generally preferred cyclically constrained β-amino acids have the α-position and β-position carbon atoms in the backbone incorporated into a substituted or unsubstituted $C_5$ to $C_8$ cycloalkyl, cycloalkenyl, or heterocycle moiety having one or more N, S, or O atoms as the heteroatom. Within any given GLP analog, the cyclically constrained β-amino acid residues may be the same or different.

DMSO=dimethylsulfoxide.

ELISA=enzyme-linked immunosorbant assay.

GLP-1=glucagon-like peptide-1.

GLP-1R=glucagon-like peptide-1 receptor.

GPCR=G protein-coupled receptor.

GTT=glucose tolerance test.

IBMX=3-isobutyl-1-methylxanthine.

KRB=Krebs Ringer Buffer.

MALDI-TOF-MS=matrix-assisted laser desorption/ionization time-of-flight mass spectrometry.

TBS=tris-buffered saline (i.e., tris(hydroxymethyl)aminomethane).

TFA=trifluoroacetic acid.

The amino acid residues in the compounds disclosed herein may either be present in their D or their L configuration. The terms "peptide" and "polypeptide" are used synonymously and refer to a polymer amino acids which are linked via an amide linkages.

"Pharmaceutically suitable salts" means salts formed with acids or bases the addition of which does not have undesirable effects when administered to mammals, including humans. Preferred are the salts with acids or bases listed in the U.S. Pharmacopoeia (or any other generally recognized pharmacopoeia) for use in humans. A host of pharmaceutically-suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene bis b hydroxynaphthoates, gentisates, isethionates, di p toluoyltartrates, methane sulphonates, ethanesulphonates, benzenesulphonates, p toluenesulphonates, cyclohexylsulphamates, quinates, and the like. Base addition salts include those derived from alkali or alkaline earth metal bases or conventional organic bases, such as triethylamine, pyridine, piperidine, morpholine, N methylmorpholine, and the like. Other suitable salts are found in, for example, Handbook of Pharmaceutical Salts, P. H. Stahl and C. G. Wermuch, Eds., © 2002, Verlag Helvitica Chemica Acta (Zurich, Switzerland) and S. M. Berge, et al., "Pharmaceutical Salts," *J. Pharm. Sci.,* 66: p. 1-19 (January 1977), both of which are incorporated herein by reference.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in synthetic organic chemistry, pharmacy, pharmacology, and the like.

Overview:

GLP-1R is a member of the B-family of G protein-coupled receptors (GPCRs).[8,9] The natural agonists for these receptors are large peptides (≥27 residues), including hormones that control many vital physiological functions. Modulators of B-family GPCR signaling are prized as pharmaceutical targets, but extensive efforts to develop agonists or antagonists of low molecular weight have yielded little success. Natural and modified peptides, on the other hand, have proven to be effective as therapeutic agents,[10,11] although rapid proteolysis poses a significant challenge in terms of optimizing pharmacological properties.[12,13] Two GLP-1R agonist peptides have been approved in the United States for treatment of type 2 diabetes, exenatide and liraglutide.[10,11] The active agent in exenatide is exendin-4, a GLP-1R agonist found in the saliva of the Gila monster.[14] Exenatide must be injected daily for therapeutic effect, but encapsulation in slowly-dissolving polymer microparticles has recently enabled weekly dosing.[15] Liraglutide is a derivative of GLP-1 that bears a hydrophobic appendage, which is intended to increase lifetime in the bloodstream by causing the peptide to bind to blood proteins.[11]

The C-terminal segments of agonist peptides are α-helical when bound to B-family GPCRs.[16] Many groups have explored side-chain crosslinking strategies to stabilize bioactive α-helices.[17-22] In addition to enhancing affinity for the intended binding partner, helix stabilization can suppress cleavage by proteases, which usually bind to extended conformations of peptide substrates. Crosslinks have most commonly been generated via lactam formation, e.g., between Lys and Glu side chains, but purely hydrocarbon crosslinks generated via alkene metathesis have become popular as well.[23-27] The first example of a helix-promoting side chain crosslink involved a B-family GPCR agonist (a lactam analog of growth hormone-releasing factor).[17] Derivatives of several B-family GPCR agonists containing lactams in the C-terminal regions have subsequently been reported,[20,22] including examples based on GLP-1.[28,29]

Design and Receptor-Activation Assays:

Described herein are potent GLP-1R agonists created by replacing selected α-amino acid residues with helix-promoting β-amino acid residues as an alternative to introducing external buttresses to stabilize the α-helical conformation. See FIG. 1 for several non-limiting, working examples of GLP-1 analogs according to the present invention. As shown in FIG. 1, the inserted β-amino acid residues may be linear, or may be conformationally constrained by a cyclic group encompassing the α and β backbone carbon atoms of the inserted β-amino acid residue. Two natural agonists of GLP-1R are known, GLP-1(7-36)-$NH_2$ and GLP-1(7-37).[35] The closely related peptide GLP-1(7-37)-$NH_2$ displays full activity[36] and has been used for systematic evaluation of i,i+4 side chain lactam placement in the segment spanned by residues 18 and 30. (Note that by convention, the N-terminal residue of native GLP-1 is designated position 7).[28] Lactams involving positions 18, 22, 26 and 30 are well tolerated in terms of agonist activity. The derivative of GLP-1(7-37)-$NH_2$ containing $\alpha \rightarrow \beta^3$ modifications at positions 26, 30 and 34 was prepared (FIG. 1, SEQ. ID. NO: 2, positions 20, 24, and 28.) (N.B.: In the attached Sequence Listing, the residue numbering starts with "1" rather than "7," which is the convention for GLP-1. Thus, the position numbering in the Sequence Listing is shifted −6 as compared to the conventional GLP-1 nomenclature which designates the N-terminal residue of GLP-1 as position 7.) SEQ. ID. NO: 2 maintains the side chain sequence of the prototype α-peptide (FIG. 1, SEQ. ID. NO: 1), but each $\beta^3$ residue contains an additional backbone $CH_2$ unit relative to the α residue it replaced. α/β-Peptide SEQ. ID. NO: 2 was compared to GLP-1(7-36)-$NH_2$ for the ability to activate human GLP-1R using a previously described cell-based assay in which agonist-stimulated cAMP production is monitored.[29,38] GLP-1 itself is a very potent agonist ($EC_{50}$=1.6±0.2 nM), as is well known. SEQ. ID. NO: 2 ($EC_{50}$>100 nM; modest cAMP production at 100 nM) while less active the GLP-1 itself, exhibited agonist activity at nM-level concentration.

From this start, α/β-peptide SEQ. ID. NO: 3 was prepared. SEQ. ID. NO: 3 is an analog of SEQ. ID. NO: 2, but contains three cyclically-constrained β residues. The cyclic constraints limit the conformations that SEQ. ID. NO: 3 can adopt as compared to the entirely linear analog SEQ. ID. NO: 2. SEQ. ID. NO: 3 as constructed in a rational effort to improve agonist activity by increasing the conformational rigidity of the peptide analog. Lys34 (SEQ. ID. NO: 3, residue 28) of GLP-1 was replaced with APC in SEQ. ID.

NO: 3 to maintain the cationic charge of the side chain, but Ala30 (residue 24) and Lys26 (residue 20) were replaced with uncharged ACPC. Because Lys26 can be used to generate lactam derivatives of GLP-1 that retain high activity,[28] the present inventors concluded that cationic charge was not necessary at this position. The α/β-peptide shown in SEQ. ID. NO: 3 proved to be a full agonist of GLP-1R, with potency comparable to that of GLP-1 itself. See Table 1.

TABLE 1

In vitro GLP1-R activation in HEK293 cells monitored by cAMP production.

| | $EC_{50}$ nM | Max Response (% GLP-1 max) |
|---|---|---|
| GLP-1(7-36)-$NH_2$ (SEQ. ID. NO: 1) | 1.6 +/− 0.2 | N.A. |
| (SEQ. ID. NO: 2) | >100 | — |
| (SEQ. ID. NO: 3) | 0.7 +/− 0.1 | 100 |
| (SEQ. ID. NO: 4) | 2.0 +/− 0.1 | 85 |
| (SEQ. ID. NO: 5) | 4.0 +/− 0.5 | 103 |
| (SEQ. ID. NO: 6) | >100 | — |
| (SEQ. ID. NO: 7) | 3.2 +/− 0.3 | 88 |

N.A. = not applicable

The favorable activity of SEQ. ID. NO: 3 prompted extending the αααβ substitution pattern toward the N-terminus via progressive introduction of ACPC residues in place of Gly22 (SEQ. ID. NO: 4, residue 16), Ser18 (SEQ. ID. NO: 5, residue 12) and Ser14 (SEQ. ID. NO: 6, residue 8). The α/β-peptides containing four or five α→β modifications (SEQ. ID. NOS: 4 and 5) were full agonists of GLP-1R with activities comparable to that of GLP-1 (Table 1). Introducing a sixth α→β modification reduced agonist activity; only a small amount of cAMP production was stimulated by 100 nM α/β-peptide SEQ. ID. NO: 6. The receptor-bound conformation of the N-terminal segment of GLP-1 is as yet unknown, but is probably not α-helical.[16] While not being limited to any underlying mechanism or mode of action, ACPC tends to induce an α-helix-like conformation. Thus, the difference in agonist activity between SEQ. ID. NO: 5 and SEQ. ID. NO: 6 suggests that the functional boundary between helical and non-helical portions of GLP-1 occurs within residues 14-17 (residues 8 and 11 in the Sequence Listing).

Peptidase Assays and Further Design:

GLP-1 is rapidly degraded in vivo, which limits the period over which exogenously added hormone can exert a physiological effect.[40,41] Proteolysis is mediated by at least two enzymes, dipeptidyl peptidase-4 (DPP-4),[40] which specifically cleaves after Ala8, and neprilysin (NEP 24.11), which cleaves after Asp15, Ser18, Tyr19, Glu27, Phe28 and Trp31.[41] It was hypothesized that the β residues in SEQ. ID. NO: 5 would suppress neprilysin action at all sites except perhaps the one closest to the N-terminus (Asp15-Val16). It was further hypothesized that SEQ. ID. NO: 5 would be highly susceptible to DPP-4 cleavage because there are no β residues near the N-terminus. Replacement of Ala8 with Aib is well-known to suppress DPP-4 activity without affecting GLP-1R agonist activity.[42] It was hypothesized that replacing Val16 with Aib (SEQ. ID. NO: 14, residue 10) would exert a comparable suppression of cleavage at the adjacent neprilysin site. The GLP-1(7-37)-$NH_2$ analog in which Aib replaces Val at position 16 displayed native-like efficacy and potency in the GLP-1R activation assay. See Table 4 in the Examples; compare the first and last entries.

α/β-Peptide SEQ. ID. NO: 7, which contains the five α→cyclic β backbone modifications of SEQ. ID. NO: 5 along with Aib modifications at positions 8 and 16 (SEQ. ID. NO: 7, residues 2 and 10), proved to be a full agonist at GLP-1R, with native-like potency (Table 1). In addition, this α/β-peptide analog of GLP-1(7-37)-$NH_2$ is highly resistant to in vitro degradation by the enzymes that cleave GLP-1 itself. See the Examples and FIGS. 7, 8, and 10. No cleavage of SEQ. ID. NO: 7 by DPP-4 could be detected over seven days under conditions that result in a 13.5 min half-life of GLP-1(7-37)-$NH_2$. More significantly, SEQ. ID. NO: 7 displayed a half-life of 83 hr in the presence of neprilysin under conditions[29] that lead to a 20 min half-life of GLP-1.

Glucose-Stimulated Insulin Secretion from Pancreatic Islets.

A critical physiological role of GLP-1 is to augment glucose-stimulated insulin secretion (GSIS) from pancreatic islet β cells. α/β-Peptide SEQ. ID. NO: 7 and GLP-1(7-36)-$NH_2$ were compared for the ability to promote GSIS from freshly isolated mouse islets. The results are depicted in FIG. 2. Administering both compounds resulted in a dose-dependent increase in GSIS, yielding ~2-fold greater insulin secretion at 90 nM agonist ($p<0.03$). It is noteworthy that the dose-dependence observed for the α/β-peptide matched that of GLP-1, which is consistent with the similarity in $EC_{50}$ values for activation of GLP-1R reported in Table 1. Residual islet insulin content values were not significantly different between islets treated with GLP-1 and those treated with SEQ. ID. NO: 7. See Examples, Table 5, and FIG. 11. This indicates that the effect of the α/β-peptide is not simply due to GLP-1 release via damaging of β cell membranes.

Figure 3A:
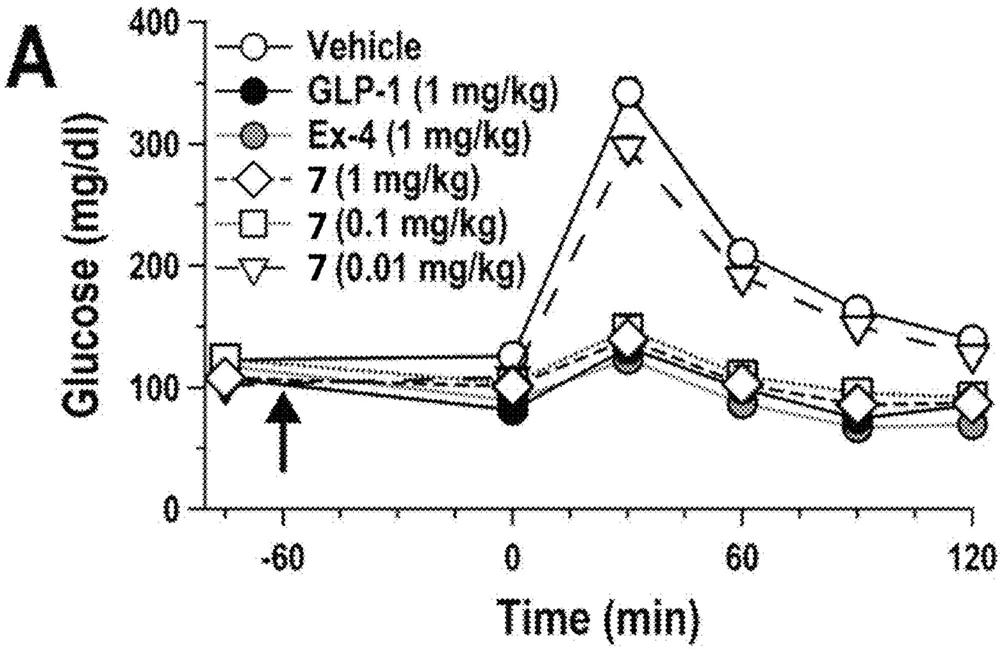
FIG. 3A: Plasma glucose values during a glucose tolerance test (GTT) for mice treated with GLP-1(7-37)-$NH_2$ (SEQ. ID. NO: 1) (1 mg/kg), exendin-4 (Ex-4, 1 mg/kg), varying doses (0.01 to 1 mg/kg) of α/β-peptide SEQ. ID. NO: 7 or vehicle. Upward arrow indicates timing of the peptide treatments delivered via IP injection. Results show mean (±SEM) of four (4) separate mice per condition.
Figure 3B:
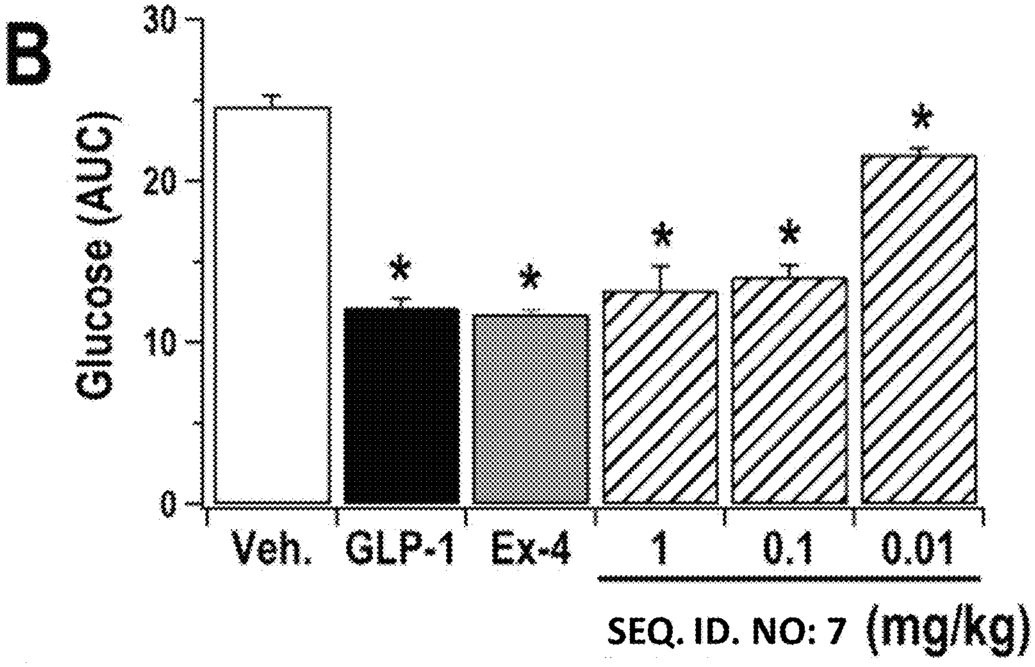
FIG. 3B: Average area under the curve (AUC) values for the GTT data shown in FIG. 3A.

Glucose Tolerance In Vivo:

The ability of α/β-peptide SEQ. ID. NO: 7 to augment insulin secretion from mouse pancreatic islets in response to elevated glucose led to an evaluation of the activity of this GLP-1 analog in vivo via glucose tolerance tests (GTT), the results of which are presented in FIGS. 3A, 3B, and 3C. In addition to the α/β-peptide and GLP-1(7-37)-$NH_2$, these studies included exendin-4 (39 residues), all three of which were tested for the ability to normalize circulating glucose levels. GLP-1, exendin-4 and α/β-peptide SEQ. ID. NO: 7 were compared at a dose of 1 mg/kg, and descending doses were examined for the α/β-peptide. For mice injected with vehicle rather than peptide (negative control), the intraperitoneal glucose challenge caused a rapid rise in blood glucose concentration that subsides after 30 min (FIGS. 3A and 3B). Mice injected with GLP-1, exendin-4 or α/β-peptide SEQ. ID. NO: 7 at 1 mg/kg showed a dramatic suppression in the rise of glucose relative to vehicle-treated mice during the GTT; the three compounds were equally effective at this dose. Dose-response behavior was observed for SEQ. ID. NO: 7 with glucose control maintained at 0.1 mg/kg, but not at 0.01 mg/kg.

Figure 3C:
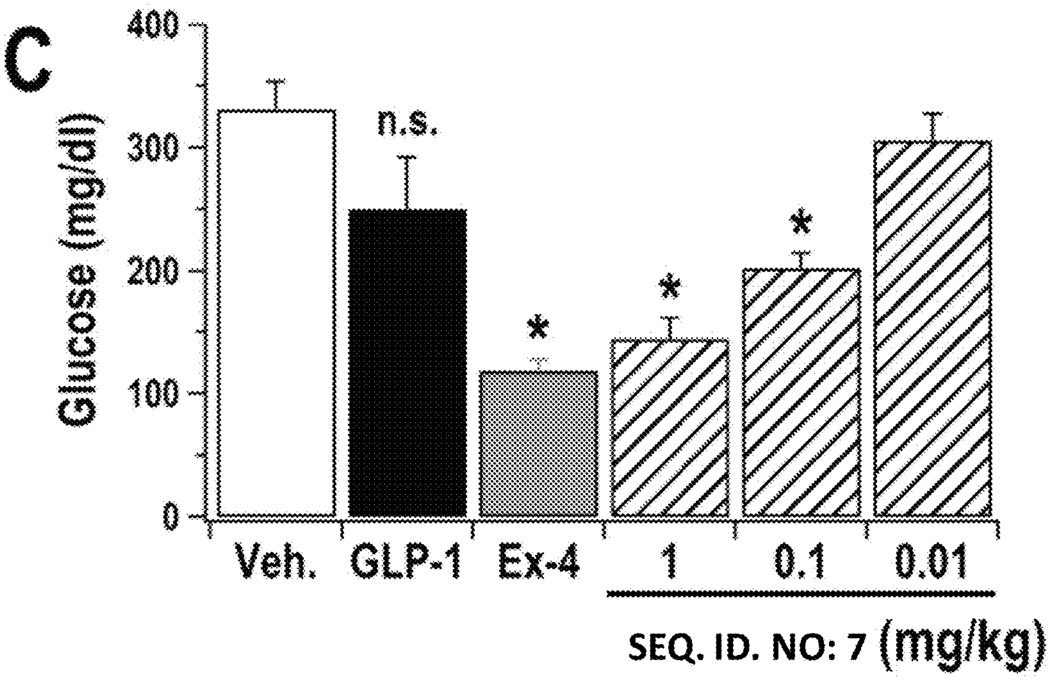
FIG. 3C: Plasma glucose values at 30 min following a second GTT that was conducted 5 hr following that shown in FIG. 3A. *, $P<0.05$ vs vehicle.

In order to determine whether the GLP-1R agonists display prolonged action, the GTT was repeated 5 hours after agonist administration. The results are shown in FIG. 3C. Mice treated with GLP-1(7-37)-$NH_2$ showed no significant difference from those treated with vehicle 30 min after the second glucose challenge; this result is expected based on the rapid enzymatic inactivation of GLP-1 in vivo. In contrast, the glucose-lowering effect of exendin-4 is maintained at 5 hr, which is consistent with prior observations. Exendin-4 persists longer in the bloodstream than does GLP-1 because exendin-4 is not cleaved by DPP-4 and is only very slowly degraded by neprilysin or other peptidases.[12,13] α/β-Peptide SEQ. ID. NO: 7 exerted the same glucose-lowering effect at 5 hours as exendin-4 (each at 1 mg/kg). The ability of SEQ. ID. NO: 7 to induce control of blood glucose levels at 5 hours was manifested even when the α/β-peptide was administered at 0.1 mg/ml. These results presumably reflect the resistance of this α/β-peptide to degradation by either DPP-4 or neprilysin.

Nutritional Compositions:

The present disclosure includes nutritional compositions. Such compositions include any food or preparation for human consumption (including for enteral or parenteral consumption) which when taken into the body (a) serve to nourish or build up tissues or supply energy and/or (b) maintain, restore or support adequate nutritional status or metabolic function.

The nutritional composition comprises at least one GLP-1 derivative as described herein and may either be in a solid or liquid form. Additionally, the composition may include edible macronutrients, vitamins and minerals in amounts desired for a particular use. The amount of such ingredients will vary depending on whether the composition is intended for use with normal, healthy infants, children or adults having specialized needs such as those which accompany hyperglycemic metabolic conditions.

Examples of macronutrients which may be added to the composition include but are not limited to edible fats, carbohydrates and proteins. Examples of such edible fats include but are not limited to coconut oil, soy oil, and mono- and diglycerides. Examples of such carbohydrates include but are not limited to glucose, edible lactose and hydrolyzed search. Additionally, examples of proteins which may be utilized in the nutritional composition include but are not limited to soy proteins, electrodialysed whey, electrodialysed skim milk, milk whey, or the hydrolysates of these proteins.

With respect to vitamins and minerals, the following may be added to the nutritional compositions described herein: calcium, phosphorus, potassium, sodium, chloride, magnesium, manganese, iron, copper, zinc, selenium, iodine, and Vitamins A, E, D, C, and the B complex. Other such vitamins and minerals may also be added.

Examples of nutritional compositions disclosed herein include but are not limited to infant formulas, dietary supplements, dietary substitutes, and rehydration compositions. Nutritional compositions of particular interest include but are not limited to those utilized for enteral and parenteral supplementation for infants, specialist infant formulas, supplements for the elderly, and supplements for those with hyperglycemia.

The nutritional composition of the present invention may also be added to food even when supplementation of the diet is not required. For example, the composition may be added to food of any type including but not limited to margarines, modified butters, cheeses, milk, yoghurt, chocolate, candy, snacks, salad oils, cooking oils, cooking fats, meats, fish and beverages.

In a preferred version, the nutritional composition is an enteral nutritional product, more preferably, an adult or pediatric enteral nutritional product. This composition may be administered to adults or children experiencing stress or having specialized needs due to chronic or acute disease states. The composition may comprise, in addition to GLP-1 analogs described herein, macronutrients, vitamins and minerals as described above. The macronutrients may be present in amounts equivalent to those present in human milk or on an energy basis, i.e., on a per calorie basis.

Methods for formulating liquid or solid enteral and parenteral nutritional formulas are well known in the art. An enteral formula, for example, may be sterilized and subsequently utilized on a ready-to-feed (RTF) basis or stored in a concentrated liquid or powder. The powder can be prepared by spray drying the formula prepared as indicated above, and reconstituting it by rehydrating the concentrate. Adult and pediatric nutritional formulas are well known in the art and are commercially available (e.g., Similac®-brand and Ensure®-brand formulas from Ross Products Division, Abbott Laboratories, Columbus, Ohio). A GLP-1 analog produced in accordance with the present disclosure may be added to commercial formulas of this type.

The energy density of the nutritional compositions in liquid form may range from about 0.6 Kcal to about 3 Kcal per ml. When in solid or powdered form, the nutritional supplements may contain from about 1.2 to more than 9 Kcals per gram, preferably about 3 to 7 Kcals per gm. In general, the osmolality of a liquid product should be less than 700 mOsm and, more preferably, less than 660 mOsm.

Pharmaceutical Compositions:

Also disclosed herein are pharmaceutical compositions comprising one or more of the GLP-1 analogs or a pharmaceutically suitable salt thereof as described herein. More specifically, the pharmaceutical composition may comprise one or more of the GLP-1 analogs as well as a standard, well-known, non-toxic pharmaceutically suitable carrier, adjuvant or vehicle such as, for example, phosphate buffered saline, water, ethanol, polyols, vegetable oils, a wetting agent or an emulsion such as a water/oil emulsion. The composition may be in either a liquid, solid or semi-solid form. For example, the composition may be in the form of a tablet, capsule, ingestible liquid or powder, injectible, suppository, or topical ointment or cream. Proper fluidity can be maintained, for example, by maintaining appropriate particle size in the case of dispersions and by the use of surfactants. It may also be desirable to include isotonic agents, for example, sugars, sodium chloride, and the like. Besides such inert diluents, the composition may also include adjuvants, such as wetting agents, emulsifying and suspending agents, sweetening agents, flavoring agents, perfuming agents, and the like.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art of pharmacy. For example, GLP-1 analogs produced as described herein can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant GLP-1 analog.

For intravenous administration, the GLP analogs may be incorporated into commercial formulations such as Intralipid©-brand fat emulsions for intravenous injection. ("Intralipid" is a registered trademark of Fresenius Kabi AB, Uppsalla, Sweden.) Where desired, the individual components of the formulations may be provided individually, in kit form, for single or multiple use. A typical intravenous dosage of a representative GLP-1 analog as described herein is from about 0.1 mg to 100 mg daily and is preferably from 0.5 mg to 3.0 mg daily. Dosages above and below these stated ranges are specifically within the scope of the claims.

Possible routes of administration of the pharmaceutical compositions include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant. The route of administration will, of course, depend upon the desired effect and the medical stated of the subject being treated. The dosage of the composition to be administered to the patient may be determined by one of ordinary skill in the art and depends upon various factors such as weight of the patient, age of the patient, immune status of the patient, etc., and is ultimately at the discretion of the medical professional administering the treatment.

With respect to form, the composition may be, for example, a solution, a dispersion, a suspension, an emulsion or a sterile powder which is then reconstituted. The composition may be administered in a single daily dose or multiple doses.

The present disclosure also includes treating hyperglycemic disorders in mammals, including humans, by administering an anti-hyperglycemic-effective amount of one or more the GLP-1 analogs described herein. In particular, the compositions of the present invention may be used to treat diabetic conditions of any and all description. Additionally, the compositions of the present invention may also be used to prevent the apoptotic death of β cells in the pancreas. To the extent the compositions impart a feeling of satiation, the compositions may also be used to treat obesity and to ease weight loss.

It should be noted that the above-described pharmaceutical and nutritional compositions may be utilized in connection with non-human animals, both domestic and non-domestic, as well as humans.

EXAMPLES

The following Examples are included to provide a more complete description of the invention disclosed and claimed herein. The Examples do not limit the scope of the claims in any fashion.

Peptide Synthesis:

Peptides were prepared on NovaPEG rink amide resin (NovaBiochem, a wholly owns subsidiary of Merck KGaA, Darmstadt, Germany) using previously reported microwave-assisted conditions for Fmoc-based solid-phase peptide synthesis.[30-33,37] After the chain had been assembled, peptides were cleaved from the resin and side chains were deprotected by treating the resin with 2 mL trifluoroacetic acid (TFA), 50 μL water, and 50 μL triisopropylsilane for 3 hr. The TFA solution was then dripped into cold ether to precipitate the deprotected peptide. Peptides were purified on a prep-C18 column (Sigma-Aldrich, St. Louis, Mo.) using reverse phase-HPLC. Purity was assessed by RP-HPLC (solvent A: 0.1% TFA in water, solvent B: 0.1% TFA in acetonitrile, C18 analytical column (4.6×250 mm), flow rate 1 mL/min, gradient 10-60% B solvent over 50 minutes). Masses were measured by MALDI-TOF-MS. See Table 2. Exendin-4 was purchased from Anaspec (Fremont, Calif.; catalog #24463).

TABLE 2

MALDI-TOF-MS data; expected and observed values (monoisotropic [M + H]$^+$)

| | Expected Mass (M + H) (m/z) | Observed Mass (m/z) |
|---|---|---|
| GLP-1(7-37)-$NH_2$ | 3353.7 | 3353.2 |
| SEQ. ID. NO: 2 | 3395.7 | 3395.8 |
| SEQ. ID. NO: 3 | 3360.6 | 3361.8 |
| SEQ. ID. NO: 4 | 3414.7 | 3414.7 |
| SEQ. ID. NO: 5 | 3438.7 | 3439.1 |
| SEQ. ID. NO: 6 | 3462.8 | 3463.3 |
| SEQ. ID. NO: 7 | 3438.7 | 3438.3 |
| SEQ. ID. NO: 8 | 3339.6 | 3341.0 |
| SEQ. ID. NO: 9 | 3307.6 | 3307.9 |

cAMP Assay:

GLP-1R activation was monitored via cAMP production.[29] cAMP accumulation was assessed in subconfluent cultures of HEK293 cells stably expressing the human GLP-1 receptor. A phosphodiesterase inhibitor, 3-isobutyl-1-methylxanthine (IBMX), was added to prevent the degradation of cAMP. For dose-response experiments, cells were treated with a peptide for 20 min at 37° C.[29] The reactions were quenched with trichloroacetic acid (1.2 M), and cAMP was isolated by the two-column chromatographic method.[38] The potency of a peptide ($EC_{50}$ value) was determined by sigmoidal curve fitting using GraphPad Prism version 5.0 (GraphPad Software, La Jolla, Calif.). See Table 3.

TABLE 3

GLP-1R activation, as measured by cAMP production, for GLP-1(7-36)-$NH_2$ and SEQ. ID. NOS: 3-7

| | AVERAGES at M Concentrations | | | | | | | |
|---|---|---|---|---|---|---|---|---|
| | −13 | −12 | −11 | −10 | −9 | −8 | −7 | $EC_{50}$ (nM) |
| GLP-1 | 4.463112 | 8.121376 | 12.55169 | 25.1881 | 43.30864 | 78.0983 | 100 | 1.6 ± 0.2 |
| 7 | 3.831377 | 2.812731 | 3.503578 | 4.469353 | 35 | 63.0221 | 88.32258 | 3.2 ± 0.3 |
| 3 | 5.122 | 12.98423 | 9.462563 | 12.26458 | 55.7495 | 89.12877 | 99.98469 | 0.7 ± 0.1 |
| 4 | 4.23 | 12.05 | 15.12 | 25.49186 | 37.89101 | 80.8351 | 84.96815 | 2.0 ± 0.1 |
| 5 | 6.14 | 10.32 | 17.1878 | 17.32045 | 32.14895 | 64.92325 | 102.6341 | 4.0 ± 0.5 |
| 6 | 5.687831 | 5.687831 | 12.05 | 18.04762 | 42.7672 | 99.2328 | 100 | 1.6 ± 0.2 |

-

GLP-1R activation data, as measured by cAMP production, was also gathered for additional α- and α/β peptide analogs of GLP-1(7-37)-$NH_2$. See Table 4. The $EC_{50}$ value for the positive control, GLP-1(7-36)-$NH_2$ (SEQ. ID. NO: 10) is shown for comparison.

TABLE 4

GLP-1R activation data for additional analogs.

| | $EC_{50}$ (nM) |
|---|---|
| H-HAEGTFTSDVSSYLEGQAAKEFIAWLVKGRG-$NH_2$ (SEQ. ID. NO: 10) | 1.6 |
| H-HAEGTFTSDVSSYLEGQAAKEFIAWLVKGRG-$NH_2$ (SEQ. ID. NO: 11) | >100 |

TABLE 4-continued

GLP-1R activation data for additional analogs.

| | $EC_{50}$ (nM) |
|---|---|
| H-HAEGTFTSDVSSYLEGQAAKEFIAWLVKGRG-$NH_2$ (SEQ. ID. NO: 12) | >100 |
| H-HAEGTFTSDASSYLEGQAAKEFIAWLVKGRG-$NH_2$ (SEQ. ID. NO: 13) | >100 |
| H-HAEGTFTSDASSYLEGQAAKEFIAWLVKGRG-$NH_2$ (SEQ. ID. NO: 14) | 1.6 |

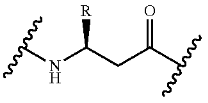

double-underlined residues

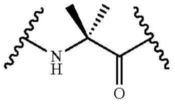

A

Protease Assays:

An HPLC method from the literature was used to assess protease action on selected compounds.[29,31] Two nmol of solid peptide was dissolved in 40 μL of TBS pH 8.0 (resulting concentration of peptide=40 μM) before protease was added. Chymotrypsin was purchased from Promega (Fitchburg, Wis.; catalog # V1062), and neprilysin was purchased from Reprokine. Ltd. (Valley Cottage, N.Y.; catalog # RKP08473); stock solutions of 250 m/mL chymotrypsin and 200 μg/mL neprilysin in water were prepared. A 10 μL aliquot of protease stock solution was added to 40 μL of 40 μM peptide solution to begin the reaction. Periodically, a 10 μL aliquot of the solution was removed, and protease action was halted by adding this aliquot to 100 μL of 1% aqueous TFA solution. A portion (100 μL) of the quenched solution was injected onto an HPLC column using the conditions described under "Peptide Synthesis", and peaks were analyzed using MALDI-TOF MS. The time course of peptide degradation was experimentally determined by integrating the area of each peak in a series of HPLC traces. The area percent of parent peptide (relative to the initial trace) was calculated for each trace and plotted in GraphPad Prism as an exponential decay to determine half-life values. See FIGS. 4-10.

Figure 4:
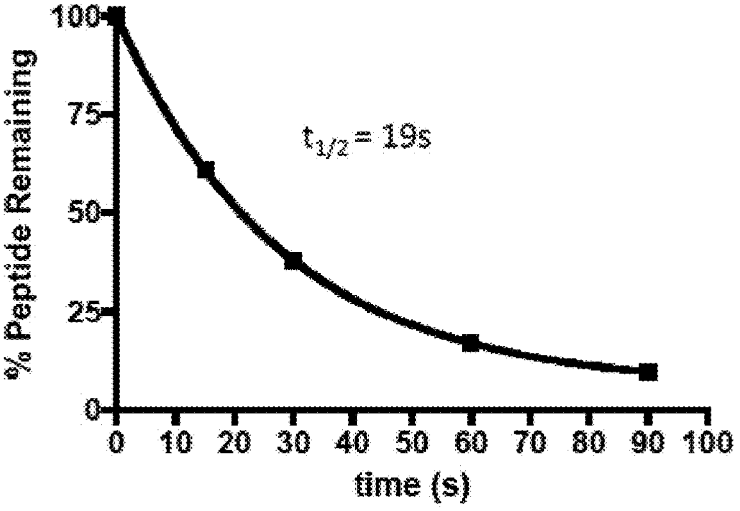
FIG. 4: Protease assay of 40 μM GLP-1(7-37)-$NH_2$ (SEQ. ID. NO: 1) with 50 μg/mL chymotrypsin in TBS pH 8.0 at room temperature. Major backbone cut sites, as determined by MALDI-TOF-MS, are indicated with double front slashes (//).
Figure 5:
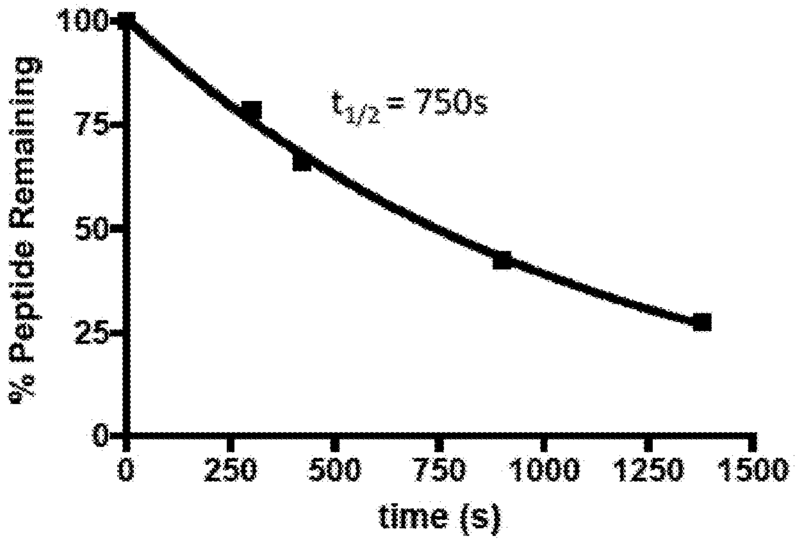
FIG. 5: Protease assay of 40 μM α/β-peptide SEQ. ID. NO: 7 with 50 μg/mL chymotrypsin in TBS pH 8.0 at room temperature. Major backbone cut site, as determined by MALDI-TOF-MS, is indicated with a double front slash.
Figure 6:
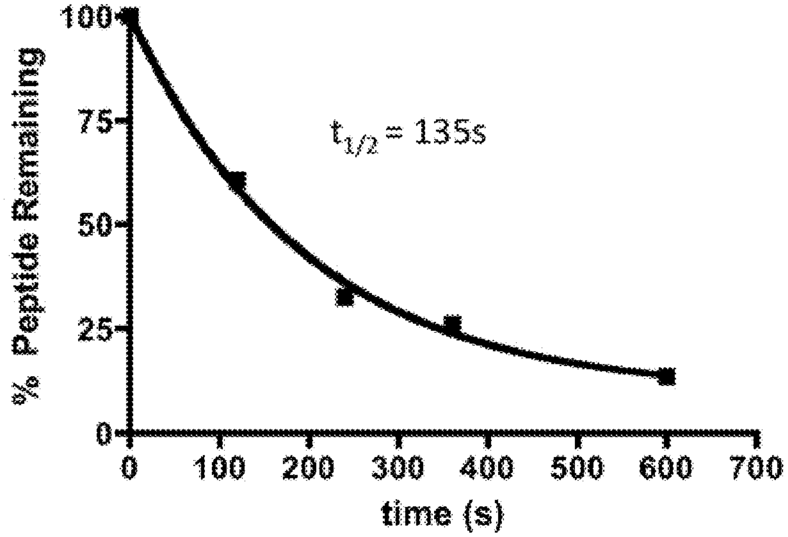
FIG. 6: Protease assay of 40 μM peptide SEQ. ID. NO: 9 with 50 μg/mL chymotrypsin in TBS pH 8.0 at room temperature. Major backbone cut sites, as determined by MALDI-TOF-MS, are indicated with double front slashes.

FIG. 4 shows the results of the protease assay for SEQ. ID. NO: 1 with 50 μg/mL chymotrypsin in TBS pH 8.0 at room temperature. Major backbone cut sites are indicated with double front slashes. As is shown in FIG. 4, less than 25% of the native GLP-1 remains after only 60 seconds of digestion. Digestion occurs at three major cleavage sites. Contrast, with FIG. 5, which shows the results of the protease assay of 40 μM α/β-peptide SEQ. ID. NO: 7 with 50 μg/mL chymotrypsin in TBS pH 8.0 at room temperature. Only one major cleavage site was apparent and more than 25% of the peptide remained when the experiment was terminated after 1500 seconds. The $t_{1/2}$ was 750 sec (as compared to 19 sec for GLP-1(7-37)-$NH_2$; FIG. 4). Compare both with FIG. 6, which shows the results of the protease assay for 40 μM peptide SEQ. ID. NO: 9 with 50 μg/mL chymotrypsin in TBS pH 8.0 at room temperature. This peptide has seven substitions, α→Aib. The $t_{1/2}$ was 135 sec.

Figure 7:
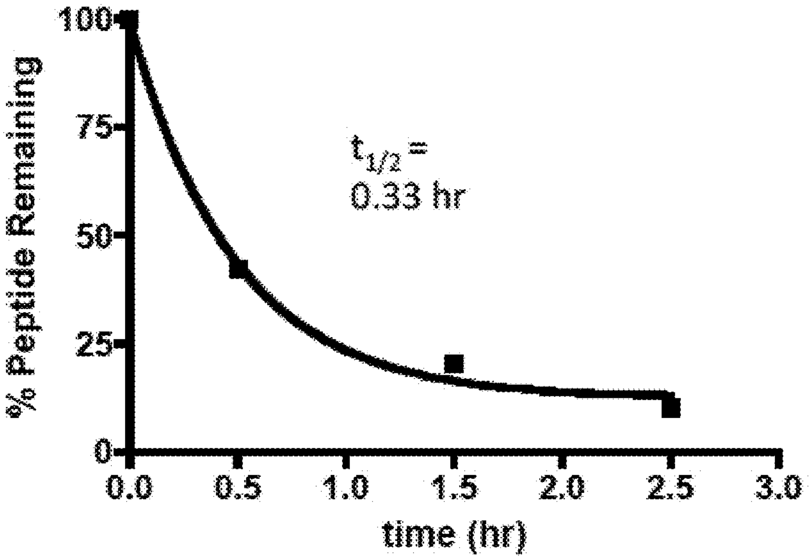
FIG. 7: Protease assay of 40 μM GLP-1(7-37)-$NH_2$ (SEQ. ID. NO: 1) with 40 μg/mL neprilysin in TBS pH 8.0 at room temperature. Major backbone cut sites, as determined by MALDI-TOF-MS, are indicated with double front slashes.
Figure 8:
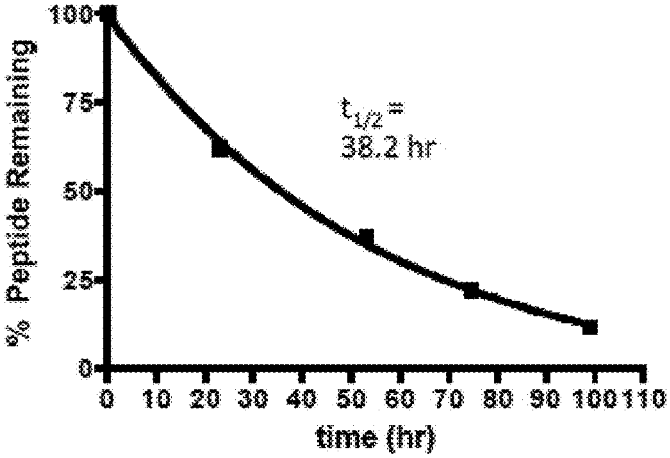
FIG. 8: Protease assay of 40 μM α/β-peptide SEQ. ID. NO: 7 with 40 μg/mL neprilysin in TBS pH 8.0 at room temperature. Major backbone cut sites, as determined by MALDI-TOF-MS, are indicated with double front slashes.

FIG. 7 shows the results of the protease assay for 40 μM GLP-1(7-37)-$NH_2$ (SEQ. ID. NO: 1) with 40 μg/mL neprilysin in TBS pH 8.0 at room temperature. Major backbone cut sites, as determined by MALDI-TOF-MS, are indicated with double front slashes. As shown in the figure, there were five major cleavage sites and the native protein had a $t_{1/2}$ of 0.33 hr. In contrast, see FIG. 8, which shows the results of the protease assay for 40 μM α/β-peptide SEQ. ID. NO: 7 with 40 μg/mL neprilysin in TBS pH 8.0 at room temperature. While there were four major cleavage sites in SEQ. ID. NO: 7, this protein retained essentially the same activity as native GLP-1, but had a $t_{1/2}$ of 38.2 hours—more than 100 times longer than the native GLP-1 peptide.

Figure 9:
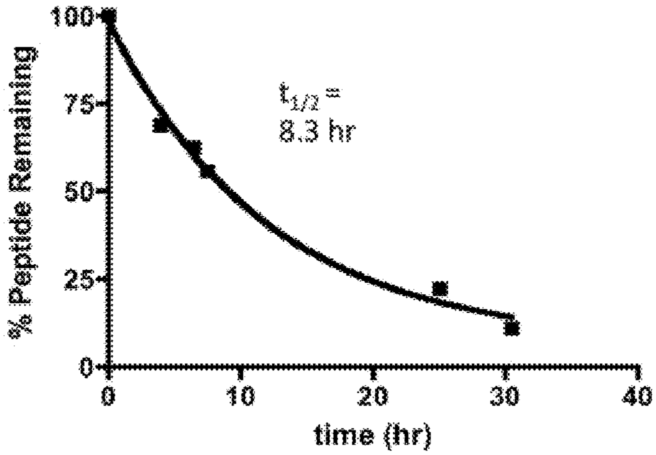
FIG. 9: Protease assay of 40 μM peptide SEQ. ID. NO: 9 with 40 μg/mL neprilysin in TBS pH 8.0 at room temperature. Major backbone cut sites, as determined by MALDI-TOF-MS, are indicated with double front slashes.
Figure 10:
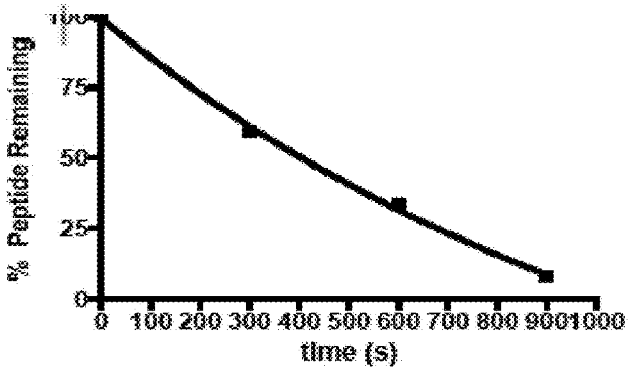
FIG. 10: Protease assay of 40 μM GLP-1(7-37)-$NH_2$ (SEQ. ID. NO: 1) with DPP-4 (EMD Biosciences, catalog #317640) in TBS pH 8.0 at 37° C. Major backbone cut site, as determined by MALDI-TOF-MS, is indicated with a double front slash.

FIG. 9 shows the results of the protease assay of 40 μM peptide SEQ. ID. NO: 9 with 40 μg/mL neprilysin in TBS pH 8.0 at room temperature. The figure shows six major cleavage sites with a $t_{1/2}$ of 8.3 hours. FIG. 10 shows the results of the protease assay of 40 μM GLP-1(7-37)-$NH_2$ (SEQ. ID. NO: 1) with DPP-4 (EMD Biosciences, catalog #317640) in TBS pH 8.0 at 37° C. Regarding FIG. 10, analogs of GLP-1(7-37)-$NH_2$ that contain Aib at position 8 are reported not to be substrates for DPP-4.[42] Thus, it was expected that SEQ. ID. NO: 7 would not be a DPP-4 substrate. To test this hypothesis, a protease assay was run using DPP-4 (EMD Biosciences; catalog #317640) as a stock solution in 20 mM Tris-HCl, 5 mM CaCl, 1 μM ZnCl, 0.05% NaN3 pH 8.0. A 10 μL aliquot of this stock solution was added to 2 nmoles of GLP-1(7-37)-$NH_2$ or SEQ. ID. NO: 7 dissolved in 40 μL of TBS buffer, pH 8.0. The DPP-4 reaction was allowed to proceed at 37° C. (higher than for the other proteases because of the low DPP-4 concentration). The half-life of GLP-1(7-37)-$NH_2$ was 13.5 minutes under these conditions. See FIG. 10. The solution containing SEQ. ID. NO: 7 and DPP-4 was monitored for seven (7) days; no cleavage was detected during this time.

Figure 11:
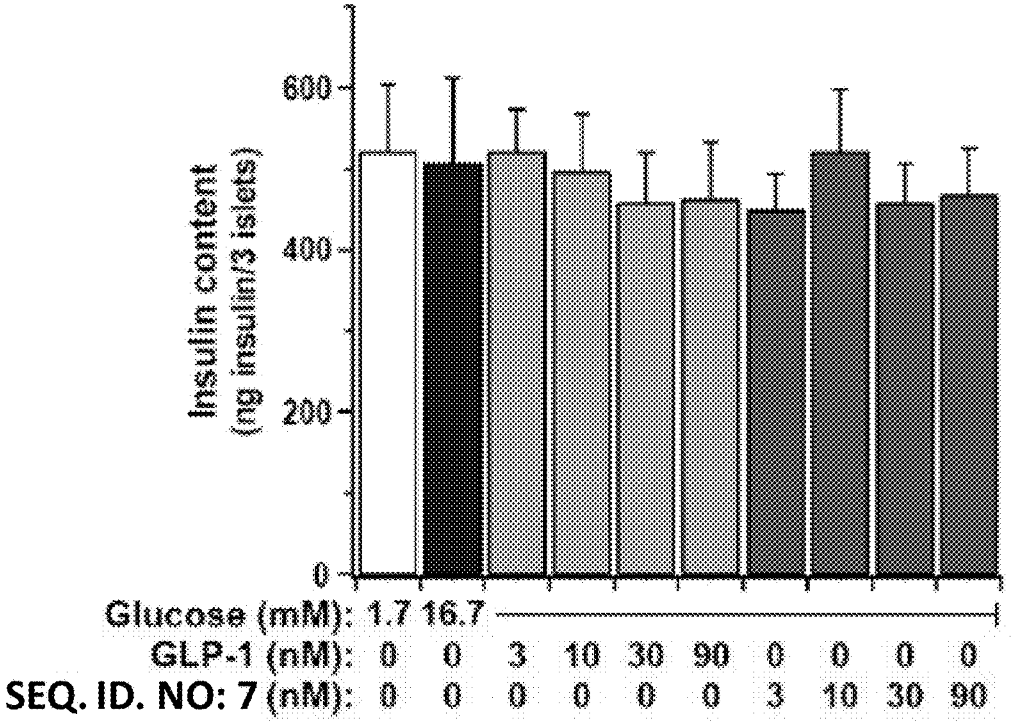
FIG. 11: Insulin content of mouse pancreatic islets after treatment with glucose and GLP-1(7-36)-$NH_2$ (SEQ. ID. NO. 1) or α/β-peptide SEQ. ID. NO: 7). The data show that insulin content in all cases is indistinguishable from insulin content of islets that have not been exposed to a GLP-1R agonist.

Islet Cell Insulin Secretion Assay:

Intact pancreatic islets were isolated from B6 mice (The Jackson Laboratory, Bar Harbor, Me.) using a collagenase digestion procedure.[48,49] Static insulin secretion assays were performed on preparations consisting of three islets incubated with GLP-1(7-36)-$NH_2$ or α/β-peptide SEQ. ID. NO: 7. Approximately 100 medium sized islets were washed three times, placed in a sterile Petri dish, and incubated overnight in culture medium (RPMI 1640, with 11.1 mM glucose, antibiotics and 10% heat-inactivated fetal bovine serum). The following day, 50 islets were washed and transferred in 100 mL of Krebs Ringer Buffer (KRB) to a Swinnex®-brand filter holder (EMD Millipore, Billerica, Mass.). The islets were sandwiched between two layers of Bio-Gel P-2 bead (Bio-Rad, Hercules, Calif.) solution (200 mg beads/mL in KRB; bottom layer, 150 mL and top layer, 300 mL). The Swinnex filter holder was attached in-line with a Minipuls®-brand pump (Gilson, Middleton, Wis.) and a FC 204 Fraction Collector (Gilson). Islets were perifused at the rate of 1 mL/min, and samples were collected at 30 sec intervals. Insulin content of the islets themselves and insulin secretion were determined by ELISA. See Table 5 and FIG. 11. FIG. 11 depicts insulin content of islets after treatment with glucose and GLP-1(7-36)-$NH_2$ or α/β-peptide SEQ. ID. NO: 7. The data show that insulin content in all cases is indistinguishable from insulin content of islets that have not been exposed to a GLP-1R agonist.

TABLE 5

Insulin secretion from mouse pancreatic islets stimulated with external GLP-1(7-36)-$NH_2$ or α/β-SEQ. ID. NO: 7.

| condition | nM concentration of peptide | Insulin Content average (ng/3 islets) | Insulin Content sem |
|---|---|---|---|
| Low glucose (LG) | 0 | 522.7 | 81.0 |
| High glucose (HG) | 0 | 508.9 | 103.5 |
| HG + 3 nM GLP-1 | 3 | 522.1 | 51.8 |
| HG + 10 nM GLP-1 | 10 | 496.4 | 70.9 |
| HG + 30 nM GLP-1 | 30 | 458.6 | 61.0 |
| HG + 90 nM GLP-1 | 90 | 463.1 | 70.3 |
| HG + 3 nM α/β-peptide 7 | 3 | 448.3 | 44.6 |
| HG + 10 nM α/β-peptide 7 | 10 | 521.4 | 76.4 |
| HG + 30 nM α/β-peptide 7 | 30 | 459.3 | 46.8 |
| HG + 90 nM α/β-peptide 7 | 90 | 467.5 | 58.5 |

Glucose Tolerance Test (GTT):

GLP-1(7-37)-$NH_2$, exendin-4 or α/β-peptide SEQ. ID. NO: 7 was administered to mice by interperitoneal (i.p.) injection at a 1 mg/kg dose, or lower for SEQ. ID. NO: 7, using an injection volume of 10 mL/kg body mass. Each peptide was first dissolved in prefiltered DMSO at 10 mg/mL concentration, then diluted >20-fold with TBS buffer, pH 7.4 (final DMSO conc.=<5%). Glucose was administered by i.p. injection with a sterile-filtered 30% D-glucose-saline solution at a 1.5 g/kg dose using a 5 mL/kg injection volume.

Thirteen-week-old male C57BL/6J mice (The Jackson Laboratory) (n=4) were fasted overnight on wood chip bedding for 15 hours prior to the experiment. Blood glucose levels were monitored from a tail tip bleed using an ACCU-CHEK®-brand blood glucose meter (Roche Diagnostics, Indianapolis, Ind.). Fasting glucose levels were measured at 75 minutes prior to the glucose injection (t=−75 min), and the compound injection was performed 60 minutes prior to the glucose injection (t=−60 min). Glucose levels were measured immediately prior to the glucose injection (t=0 min) to assess any changes in the baseline glucose caused by peptide administration. Blood glucose levels were monitored at 30, 60, 90, and 120 minutes after injection of glucose.

Five hours after peptide injection, the mice received a second injection of 1.5 g/kg glucose. Blood glucose was monitored at 30 min after this second glucose injection. Mice were sacrificed by $CO_2$ inhalation at the conclusion of the GTT. The results are shown in Tables 6 and 7.

TABLE 6

Blood glucose levels in mice measured during i.p. glucose tolerance test.

| Time (min) | Average Blood Glucose Level (mg/dL) −60.0 | 0.0 | 30.0 | 60.0 | 90.0 | 120.0 |
|---|---|---|---|---|---|---|
| Vehicle | 122.8 | 126.0 | 342.5 | 210.3 | 163.5 | 139.3 |
| GLP-1(7-37)-NH2 | 108.0 | 81.8 | 132.8 | 99.3 | 74.8 | 86.0 |
| Exendin-4 | 118.0 | 89.5 | 123.5 | 87.0 | 67.5 | 70.0 |
| α/β-Peptide 7 (1 mg/kg) | 107.8 | 101.3 | 139.8 | 103.0 | 86.3 | 87.5 |
| α/β-Peptide 7 (0.1 mg/kg) | 123.5 | 103.5 | 147.8 | 110.0 | 95.5 | 92.3 |
| α/β-Peptide 7 (0.01 mg/kg) | 102.0 | 108.8 | 297.3 | 191.0 | 150.3 | 127.0 |
| α/β-Peptide 7 (0.001 mg/kg) | 117.5 | 123.5 | 291.3 | 214.0 | 158.8 | 139.3 |

TABLE 7

Average Blood Glucose Level at 30 min with Standard Deviation of the Mean (SDOM)

| | AUC | SDOM |
|---|---|---|
| Vehicle | 331.3 | 22.3 |
| GLP-1(7-37)-NH2 | 250.5 | 41.6 |
| Exendin-4 | 118.8 | 8.8 |
| α/β-Peptide 7 (1 mg/kg) | 144.3 | 20.7 |
| α/β-Peptide 7 (0.1 mg/kg) | 202.5 | 11.8 |
| α/β-Peptide 7 (0.01 mg/kg) | 306.0 | 21.5 |
| α/β-Peptide 7 (0.001 mg/kg) | 323.3 | 16.1 |

DISCUSSION

The results show that a GLP-1-derived oligomer containing multiple replacements of α-amino acid residues with conformationally constrained β-amino acid residues can maintain native-like agonist activity at the GLP-1 receptor. Replacement of native α residues with conformationally constrained β-amino acid residues yielded protease-resistant peptides that retained native-like agonist activity at the GLP-1 receptor. Replacement of native α residues with flexible $\beta^3$-homologues (e.g., SEQ. ID. NO: 2) yielded protease-resistant peptides that retained some agonist activity, but less than native GLP-1. Without being limited to any underlying mechanism, this finding is attributed to the extra degree of conformational freedom in $\beta^3$ residues relative to a residues, which increases the conformational entropy that must be lost upon adoption of the bioactive conformation. The C-terminal segment of GLP-1 is known to be α-helical in the receptor-bound state,[16] but the point at which the helix terminates in this state had been unknown. The difference in activity between α/β-peptide SEQ. ID. NO: 5 (a potent agonist) and α/β-peptide SEQ. ID. NO: 6 (which displays attenuated agonist activity) suggests that the C-terminal α-helix terminates near position 14 in the bioactive conformation of GLP-1. Ser14→Ala modification is reported not to affect GLP-1 potency,[43] so loss of the native side chain at this position in SEQ. ID. NO: 6 does not explain this α/β-peptide's lowered agonist activity.

α/β-Peptide SEQ. ID. NO: 7 mimics GLP-1 in terms of augmenting glucose-stimulated insulin secretion from pancreatic β cells and regulating blood glucose levels in vivo. The prolonged effect of this α/β-peptide relative to GLP-1 is attributed to the strongly diminished susceptibility to degradation by widely distributed peptidases, a property that arises in part from the multiple β residue replacements.

REFERENCES CITED

The following documents are incorporated herein by reference:

1. Arkin, M. R. & Wells, J. A. Small-molecule inhibitors of protein-protein interactions: progressing toward the dream. *Nat. Rev. Drug Discov.* 3, 301-17, (2004).
2. Yin, H. & Hamilton, A. D. Strategies of targeting protein-protein interactions with synthetic agents. *Angew. Chem. Int. Ed.* 44, 4130-63, (2005).
3. Azzarito, V., Long, K., Murphy, N. S., & Wilson, A. J. Inhibition of α-helix-mediated protein-protein interactions using designed molecules. *Nat. Chem.* 5, 161-73, (2013).
4. Gellman, S. H. Foldamers: A Manifesto. *Acc. Chem. Res.* 31, 173-80, (1998).

5. Goodman, C. M., Choi, S., Shandler, S., & DeGrado, W. F. Foldamers as versatile frameworks for the design and evolution of function. *Nat. Chem. Biol.* 3, 252-62 (2007).

6. Horne, W. S., & Gellman, S. H. Foldamers with heterogeneous backbones. *Acc. Chem. Res.* 41, 1399-408 (2008).

7. Guichard, H. & Huc, I. Synthetic foldamers. *Chem. Comm.* 47, 5933-41, (2011).

8. Fredriksson, R., Lagerstrom, M. C., Lundin, L. G., & Schioth, H. B. The G-protein-coupled receptors in the human genome form five main families. Phylogenetic analysis, paralogon groups, and fingerprints. *Mol. Pharmacol.* 63, 1256-72, (2003).

9. Lagerstrom, M. C. & Schioth, H. B. Structural diversity of G protein-coupled receptors and significance for drug discovery. *Nature Reviews. Drug Discovery* 7, 339-57, (2008).

10. Davidson, M. B., Bate, G. & Kirkpatrick, P. Exenatide. *Nat. Rev. Drug Discov.* 4, 713-4, (2005).

11. Drucker, D. J., Dritselis, A. & Kirkpatrick, P. Liraglutide. *Nat. Rev. Drug Discov.* 9, 267-8, (2010).

12. Gao, W. & Jusko, W. J. Target-mediated pharmacokinetic and pharmacodynamic model of exendin-4 in rats, monkeys, and humans. *Drug Metab. Dispos.* 40, 990-7, (2012).

13. Parkes, D., Jodka, C., Smith, P., Nayak, S., Rinehart, L., Gingerich, R., Chen, K. & Young, A. Pharmacokinetic actions of exendin-4 in the rat: Comparison with glucagon-like peptide-1, *Drug Dev. Res.* 53, 260-7, (2001).

14. Christel, C. M., DeNardo, D. F. & Secor, S. M. Metabolic and digestive response to food ingestion in a binge-feeding lizard, the Gila monster (Heloderma suspectum). *The Journal of Experimental Biology* 210, 3430-9, (2007).

15. Ridge, T., Moretto, T., Macconell, L., Pencek, R., Han, J., Schulteis, C. & Porter, L. Comparison of Safety And Tolerability With Continuous (Exenatide Once Weekly) Or Intermittent (Exenatide Twice Daily) Glp-1 Receptor Agonism In Patients With Type 2 Diabetes. *Diabetes Obes. Metab.* 14, 1097-1103, (2012).

16. Underwood, C. R., Garibay, P., Knudsen, L. B., Hastrup, S., Peters, G. H., Rudolph, R. & Reedtz-Runge, S. Crystal Structure of Glucagon-like Peptide-1 in Complex with the Extracellular Domain of the Glucagon-like Peptide-1 Receptor. *J. Biol. Chem.* 285, 723-30, (2010).

17. Felix, A. M., Heimer, E. P., Wang, G. T., Lambros, T. J., Fournier, A. J., Mowles, T. F., Maines, S., Campbell, R. M., Wegrzynski, B. B., Toomer, V., Fry, D., & Madison, V. S. Synthesis, biological activity and conformational analysis of cyclic GRF analogs. *Int. J. Peptide Protein Res.* 21, 441-54, (1988).

18. Ghadiri, M. R., & Choi, C. Secondary structure nucleation in peptides. Transition metal ion stabilized α-helices. *J. Am. Chem. Soc.* 112, 1630-32, (1990).

19. Jackson, D. Y., King, D. S., Chmielewski, J., Singh, S., & Schultz, P. G. General approach to the synthesis of short α-helical peptides. *J. Am. Chem. Soc.* 113, 9391-2, (1991).

20. Chorev, M., Roubini, E., McKee, R. L, Gibbons, S. W., Goldman, M. E., Caufield, M. P., & Rosenblatt, M. Cyclic parathyroid hormone related protein agonists: lysine 13 to aspartic acid 17 [i to (i+4)] side chain to side chain lactamization. *Biochemistry* 30, 5968-74, (1991).

21. Judice, J. K., Tom, J. Y. K., Huang, W., Wrin, T., Vennari, J., Petropoulos, C. J., & McDowell, R. S. Inhibition of HIV type 1 infectivity by constrained α-helical peptides: implications for the viral fusion mechanism. *Proc. Natl. Acad. Sci. USA* 94, 13426-30, (1997).

22. Trivedi, D., Lin, Y., Ahn, J. M., Siegel, M., Mollova, N. N., Schram, K. H., & Hruby, V. J. Design and synthesis of conformationally constrained glucagon analogues. *J. Med. Chem.* 43, 1714-22, (2000).

23. Blackwell, H. E. & Grubbs, R. H. Highly efficient synthesis of covalently cross-linked peptide helices by ring-closing metathesis. *Angew. Chem. Int. Ed.* 37, 3281-4, (1998).

24. Walensky, L. D., Kung, A L., Escher, I., Malia, T. J., Barbuto, S., Wright, R. D., Wagner, G., Verdine, G. L. & Korsmeyer, S. J. Activation of apoptosis in vivo by a hydrocarbon-stapled BH3 helix. *Science* 305, 1466-70, (2004).

25. Chapman, R. N., Dimartino, G. & Arora, P. S. A highly stable short α-helix constrained by main-chain hydrogen-bond surrogate. *J. Am. Chem. Soc.* 126, 12252-3, (2004).

26. Verdine, G. L. & Hilinski, G. J. Stapled peptides for intracellular drug targets. *Meth. Enzymol.* 503, 3-33, (2012).

27. Okamoto, T., Zobel, K., Fedorova, A., Quan, C., Yang, H., Fairbrother, W. J., Huang, D. C. S., Smith, B. J., Keshayes, K. & Czabotar, P. E. Stabilization the pro-apoptotic BimBH3 helix (BimSAHB) does not necessarily enhance affinity of biological activity. *ACS Chem. Biol.* 8, 297-302, (2013).

28. Miranda, L. P., Winters, K. A., Gegg, C. V., Patel, A., Aral, J., Long, J., Zhang, J., Diamond, S., Guido, M., Stanislaus, S., Ma, M., Li, H., Rose, M. J., Poppe, L., & Veniant, M. M. Design and synthesis of conformationally constrained glucagon-like peptide-1 derivatives with increased plasma stability and prolonged in vivo activity. *J. Med. Chem.* 51, 2758-65, (2008).

29. Murage, E. N., Gao, G. Z., Bisello, A., & Ahn, J. M. Development of Potent Glucagon-like Peptide-1 Agonists with High Enzyme Stability via Introduction of Multiple Lactam Bridges. *J. Med. Chem.* 53, 6412-20, (2010).

30. Horne, W. S., Boersma, M. D., Windsor, M. A. & Gellman, S. H. Sequence-Based Design of α/β-Peptide Foldamers that Mimic α-Helical BH3 Domains, *Angew. Chem. Int. Ed.* 47, 2853-6, (2008).

31. Horne, W. S., Johnson, L. M., Ketas, T. J., Klasse, P. J., Lu, M., Moore, J. P., Gellman, S. H. Structural and biological mimicry of protein surface recognition by α/β-peptide foldamers. *Proc. Natl. Acad. Sci. USA* 106, 14751-6, (2009).

32. Johnson, L. M., Mortenson, D. E., Yun, H. G., Home, W. S., Ketas, T. J., Lu, M., Moore, J. P., & Gellman, S. H. Enhancement of α-Helix Mimicry by an α/β-Peptide Foldamer via Incorporation of a Dense Ionic Side-Chain Array. *J. Am. Chem. Soc.* 134, 7317-20, (2012).

33. Boersma, M. D., Haase, H. S., Peterson-Kaufman, K. J., Lee, E. F., Clarke, O. B., Colman, P. M., Smith, B. J., Home, W. S., Fairlie, W. D., & Gellman, S. H. Evaluation of diverse α/β-backbone patterns for functional α-helix mimicry: analogues of the Bim BH3 domain. *J. Am. Chem. Soc.* 134, 315-23, (2012).

34. Johnson, L. M. & Gellman, S. H. α-Helix Mimicry with α/β-Peptides, *Meth. Enzymol.* 523, 407-29, (2013).

35. Hansen, L., Deacon, C. F., Orskov, C., & Holst, J. J. Glucagon-like peptide-1-(7-36)amide is transformed to glucagon-like peptide-1-(9-36)amide by dipeptidyl peptidase IV in the capillaries supplying the L cells of the porcine intestine. *Endocrinology* 140, 5356-63, (1999).

36. de Menthiere, C. S., Chavanieu, A., Grassy, G., Dalle, S., Salazar, G., Kervran, A., Pfieiffer, B., Renard, P., Delagrange, P., Manechez, D., Bakes, D., Ktorza, A., & Calas, B. Structure requirements of the N-terminal region of GLP-1-[7-37]-$NH_2$ for receptor interaction and cAMP production. *Eur. J. Med. Chem.* 39, 473-80, (2004).
37. Horne, W. S., Price, J. L., & Gellman, S. H. Interplay among side chain sequence, backbone composition, and residue rigidification in polypeptide folding and assembly. *Proc. Natl Acad Sci USA* 105, 9151-6, (2008).
38. Salomon, Y., Londos, C., & Rodbell, M. A highly sensitive adenylate cyclase assay. *Anal. Biochem.* 58, 541-8, (1974).
39. Price, J. L., Hadley, E. B., Steinkruger, J. D., & Gellman, S. H. Detection and Analysis of Chimeric Tertiary Structure via Backbone Thioester Exchange: Packing of an α-Helix against an α/β-Peptide Helix, *Angew. Chem. Int. Ed.* 49, 368-71, (2010).
40. Jessen, L., Aulinger, B. A., Hassel, J. L., Roy, K. J., Smith, E. P., Greer, T. M., Woods, S. C., Seeley, R. J., & D'Alessio, D. A. Suppression of food intake by glucagon-like peptide-1 receptor agonists: relative potencies and role of dipeptidyl peptidase-4. *Endocrinology* 153, 5735-45, (2012).
41. Hupe-Sodmann, K., McGregor, G. P., Bridenbaugh, R., Goke, R., Goke, B., Thole, H., Zimmermann, B., & Voigt, K. Characterisation of the processing by human neutral endopeptidase 24.11 of GLP-1(7-36) amide and comparison of the substrate specificity of the enzyme for other glucagon-like peptides. *Regul. Pept.* 58, 149-56, (1995).
42. Deacon, C. F., Knudsen, L. B., Madsen, K., Wiberg, F. C., Jacobsen, O., & Holst, J. J. Dipeptidyl peptidase IV resistant analogues of glucagon-like peptide-1 which have extended metabolic stability and improved biological activity. *Diabetologia* 41, 271-8, (1998).
43. Adelhorst, K., Hedegaard, B. B., Knudsen, L. B., & Kirk, O. Structure-activity studies of glucagon-like peptide-1. *J. Biol. Chem.* 269, 6275-8, (1994).
44. Stewart, M. L., Fire, E., Keating, A. E., & Walensky, L. D. The Mcl-1 BH3 helix is an exclusive Mcl-1 inhibitor and apoptosis sensitizer, *Nat. Chem. Biol.* 6, 595-601, (2010).
45. Phillips, C., Roberts, L. R. Schade, M., Bazin, R., Bent, A., Davies, N. L., Moore, R., Pannifer, A. D., Pickford, A. R., Prior, S. H., Read, C. M., Scott, A., Brown, D. G., Xu, B., & Irving, S. L., Design and structure of stapled peptides binding to estrogen receptors, *J. Am. Chem. Soc.* 133, 9696-9, (2011).
46. Baek, S., Kutchukian, P. S., Verdine, G. L., Huber, R., Holak, T. A., Lee, K. W., & Popowicz, G. M., Structure of the stapled p53 peptide bound to Mdm2, *J. Am. Chem. Soc.* 134, 103-6, (2012).
47. Bullock, B. N., Jochim, A. L., & Arora, P. S. Assessing helical protein interfaces for inhibitor design. *J. Am. Chem. Soc.* 133, 14220-3, (2011).
48. Bhatnagar, S.; Oler, A. T.; Rabaglia, M. E.; Stapleton, D. S.; Schueler, K. L.; Truchan, N. A.; Worzella, S. L.; Stoehr, J. P.; Clee, S. M.; Yandell, B. S.; Keller, M. P.; Thurmond, D. C.; Attie, A. D.: Positional cloning of a type 2 diabetes quantitative trait locus; tomosyn-2, a negative regulator of insulin secretion. *PLoS Genet.* 7, e1002323, (2011).
49. Rabaglia, M. E.; Gray-Keller, M. P.; Frey, B. L.; Shortreed, M. R.; Smith, L. M.; Attie, A. D.: Alpha-Ketoisocaproate-induced hypersecretion of insulin by islets from diabetes-susceptible mice. *Am. J. Physiol. Endocrinol. Metab.* 289, E218-24, (2005).

What is claimed is:

1. A composition of matter comprising an isolated, unnatural analog of glucagon-like peptide 1 (GLP-1) wherein the isolated, unnatural analog of GLP-1 comprises an amino acid sequence of a native GLP-1 wherein at least one a-amino acid residue located at least 12 residues downstream from residue 7 of the native GLP 1 is replaced with a β-amino acid residue, wherein the at least one a-amino acid residue is replaced with a cyclically constrained β-amino acid residue.

2. A composition of matter comprising an isolated, unnatural analog of glucagon-like peptide 1 (GLP-1) wherein the isolated, unnatural analog of GLP-1 comprises an amino acid sequence of a native GLP-1 wherein at least one a-amino acid residue located at least 12 residues downstream from residue 7 of the native GLP 1 is replaced with a β-amino acid residue, wherein at least two α-amino acid residues, each located at least 12 residues downstream from residue 7 of the native GLP-1, are replaced with a β-amino acid residues.

3. The composition of matter of claim 2, wherein the at least two α-amino acid residues are replaced with cyclically constrained β-amino acid residues.

4. A composition of matter comprising an isolated, unnatural analog of glucagon-like peptide 1 (GLP-1) wherein the isolated, unnatural analog of GLP-1 comprises an amino acid sequence of a native GLP-1 wherein at least one α-amino acid residue located at least 12 residues downstream from residue 7 of the native GLP 1 is replaced with a β-amino acid residue, wherein at least three α-amino acid residues, each located at least 12 residues downstream from residue 7 of the native GLP-1, are replaced with a β-amino acid residue.

5. The composition of matter of claim 4, wherein the at least three α-amino acid residues are replaced with cyclically constrained β-amino acid residues.

6. A synthetic, unnatural polypeptide having an amino acid sequence as shown in SEQ. ID: NO: 16.

7. The polypeptide of claim 6, wherein

X at position 9 is 2-aminocyclopentane carboxylic acid (ACPC);

X at position 13 is $\beta^3$-Ser or ACPC;
X at position 17 is $\beta^3$-Gly or ACPC;
X at position 21 is $\beta^3$-Lys or ACPC;
X at position 25 is ACPC; and
X at position 29 is $\beta^3$-Lys or 3-aminopyrrolidine-4-carboxylic acid.

8. The polypeptide of claim 6, wherein
X at position 9 is ACPC;
X at position 13 is ACPC;
X at position 17 is ACPC;
X at position 21 is ACPC;
X at position 25 is ACPC; and
X at position 29 is 3-aminopyrrolidine-4-carboxylic acid.

9. The polypeptide of claim 6, wherein
X at position 9 is ACPC;
X at position 13 is $\beta^3$-Ser;
X at position 17 is $\beta^3$-Gly;
X at position 21 is $\beta^3$-Lys;
X at position 25 is ACPC; and
X at position 29 is $\beta^3$-Lys.

10. A method to fabricate glucagon-like peptide-1 receptor agonists that are resistant to proteolytic degradation, the method comprising:

constructing an isolated, unnatural glucagon-like peptide 1 (GLP-1) analog having an amino acid sequence comprising a native GLP-1 sequence, but replacing at least one α-amino acid residue in the native GLP-1 sequence with a β-amino acid residue, wherein the replacement β-amino acid residue is located at least 12 residues downstream from residue 7 of the native GLP-1 sequence, wherein the at least one α-amino acid residue is replaced with a cyclically constrained β-amino acid residue.

11. A method to fabricate glucagon-like peptide-1 receptor agonists that are resistant to proteolytic degradation, the method comprising:

constructing an isolated, unnatural glucagon-like peptide 1 (GLP-1) analog having an amino acid sequence comprising a native GLP-1 sequence, but replacing at least one α-amino acid residue in the native GLP-1 sequence with a β-amino acid residue, wherein the replacement β-amino acid residue is located at least 12 residues downstream from residue 7 of the native GLP-1 sequence, wherein at least two α-amino acid residues are replaced with β-amino acid residues, and wherein each replacement β-amino acid residue is located at least 12 residues from residue 7 of the native GLP-1 sequence.

12. The method of claim 11, wherein the at least two α-amino acid residues are replaced with cyclically constrained β-amino acid residues.

13. A method to fabricate glucagon-like peptide-1 receptor agonists that are resistant to proteolytic degradation, the method comprising:

constructing an isolated, unnatural glucagon-like peptide 1 (GLP-1) analog having an amino acid sequence comprising a native GLP-1 sequence, but replacing at least one α-amino acid residue in the native GLP-1 sequence with a β-amino acid residue, wherein the replacement β-amino acid residue is located at least 12 residues downstream from residue 7 of the native GLP-1 sequence, wherein at least three α-amino acid residues are replaced with β-amino acid residues, and wherein each replacement β-amino acid residue is located at least 12 residues from residue 7 of the native GLP-1 sequence.

14. The method of claim 13, wherein the at least three α-amino acid residues are replaced with cyclically constrained β-amino acid residues.

* * * * *